United States Patent
Nguyen et al.

(10) Patent No.: US 8,313,937 B2
(45) Date of Patent: Nov. 20, 2012

(54) POLYPEPTIDE HAVING PHYTASE ACTIVITY AND NUCLEOTIDE SEQUENCE ENCODING THE SAME

(75) Inventors: Khanh Q. Nguyen, Reichelsheim (DE); Bruno Winter, Stuttgart (DE)

(73) Assignee: AB Enzymes GmbH, Darmstadt (DE)

( * ) Notice: Subject to any disclaimer, the term of this patent is extended or adjusted under 35 U.S.C. 154(b) by 1048 days.

(21) Appl. No.: 11/665,631

(22) PCT Filed: Oct. 14, 2005

(86) PCT No.: PCT/EP2005/011108
§ 371 (c)(1),
(2), (4) Date: May 20, 2008

(87) PCT Pub. No.: WO2006/042719
PCT Pub. Date: Apr. 27, 2006

(65) Prior Publication Data
US 2009/0169536 A1    Jul. 2, 2009

Related U.S. Application Data

(63) Continuation of application No. PCT/EP2005/011108, filed on Oct. 14, 2005.

(30) Foreign Application Priority Data

Oct. 15, 2004 (DE) .................. 10 2004 050 410

(51) Int. Cl.
C12N 9/16  (2006.01)
C12N 1/20  (2006.01)
C12N 15/00  (2006.01)
C07H 21/04  (2006.01)

(52) U.S. Cl. .................. 435/196; 435/252.3; 435/320.1; 536/23.2

(58) Field of Classification Search .................. 435/196, 435/252.3, 320.1; 536/23.2
See application file for complete search history.

(56) References Cited

U.S. PATENT DOCUMENTS

| 4,873,192 | A | 10/1989 | Kunkel | |
|---|---|---|---|---|
| 6,841,370 | B1 * | 1/2005 | Lei | 435/196 |
| 7,300,781 | B2 * | 11/2007 | Lei | 435/196 |
| 2003/0157646 | A1 | 8/2003 | Lanahan et al. | |
| 2004/0091968 | A1 | 5/2004 | Short et al. | |

FOREIGN PATENT DOCUMENTS

| CN | 1410540 A | 4/2003 |
|---|---|---|
| WO | 93/24621 A1 | 12/1993 |
| WO | 94/28117 A1 | 12/1994 |
| WO | 99/08539 A1 | 2/1999 |
| WO | 00/71728 A1 | 11/2000 |
| WO | 01/36607 A1 | 5/2001 |
| WO | 01/90333 A2 | 11/2001 |
| WO | 02/095003 A2 | 11/2002 |
| WO | 03/038035 A2 | 5/2003 |
| WO | 03/038111 A2 | 5/2003 |
| WO | 2004/015084 A2 | 2/2004 |

OTHER PUBLICATIONS

Seffernick et al. [J. Bacteriol. 183(8), Apr. 2001, p. 2405-2410].*
Dassa et al., 1990, J. Bacteriol. 172:5497-5500 (Accession-Nr, M58708).
Rodriguez et al., 2000, Arch. Biochem. Biophys., 382:105-112.
Garrett, et al., Applied Environ. Microbiol., 2004, 70(5), 3041-3046.
Myers, E.W. and W. Miller, 1988, CABIOS 4:1, 11-17.
Chao, K-M, W.R. Pearson and W. Miller, 1992, CABIOS 8:5, 481-487.
Kunkel, Proc. Natl. Acad. Sci. USA, 82:488 (1985).
Kunkel et al., Methods in Enzymo., 154:367 (1987).
Dayhoff et al., Atlas of Protein Sequence and Structure, Natl. Biomed. Res. Found., Washington, D.C., vol. 5, Suppl. 3, 345-352 (1978).
Pentilla et al., Gene 61:155-164, 1987.
Shoemaker et al., 1983, Bio/Technology 1, 691-696.
Hynes et al., 1983, Mol. Cell. Biol. 3:1430-1439.
Kelly and Hynes, 1985, EMBO J. 4:475-47.
Harkki et al., 1991, Enzyme Microb. Technol. 13:227-233.
Nucleic Acids Research 1989, 17(2), 723-733.
Nucleic Acids Research 1990, 18(6), 1656.
Hirschberg, D.S. 1975, Commun Assoc Comput Mach 18:341-343.
The Use of Restriction Endonucleases and T4 DNA Ligase, Techniques in Molecular Biology, pp. 198-219, Frits R, Mooi and Wim Gaastra, Mac Millan Publishing Company, New York, 1983.

* cited by examiner

*Primary Examiner* — Tekchand Saidha
(74) *Attorney, Agent, or Firm* — Edwards Wildman Palmer LLP; Peter F. Corless; Christine C. O'Day

(57) ABSTRACT

The present invention features a recombinant DNA molecule which, upon expression in a prokaryotic or eukaryotic host cell, encodes a polypeptide having phytase activity. In preferred embodiments, the recombinant DNA molecule comprises a DNA sequence selected from DNA sequences which have been obtained by variations of the mature wild-type *E. coli* phytase sequence, wherein at least one amino acid at position 200 or position 207 is mutated as compared to the wild-type sequence, where the recombinant DNA molecule is, upon expression in a suitable host cell, associated with an increased activity of the thus encoded protein in the culture supernatant.

11 Claims, 5 Drawing Sheets

Figure 1:
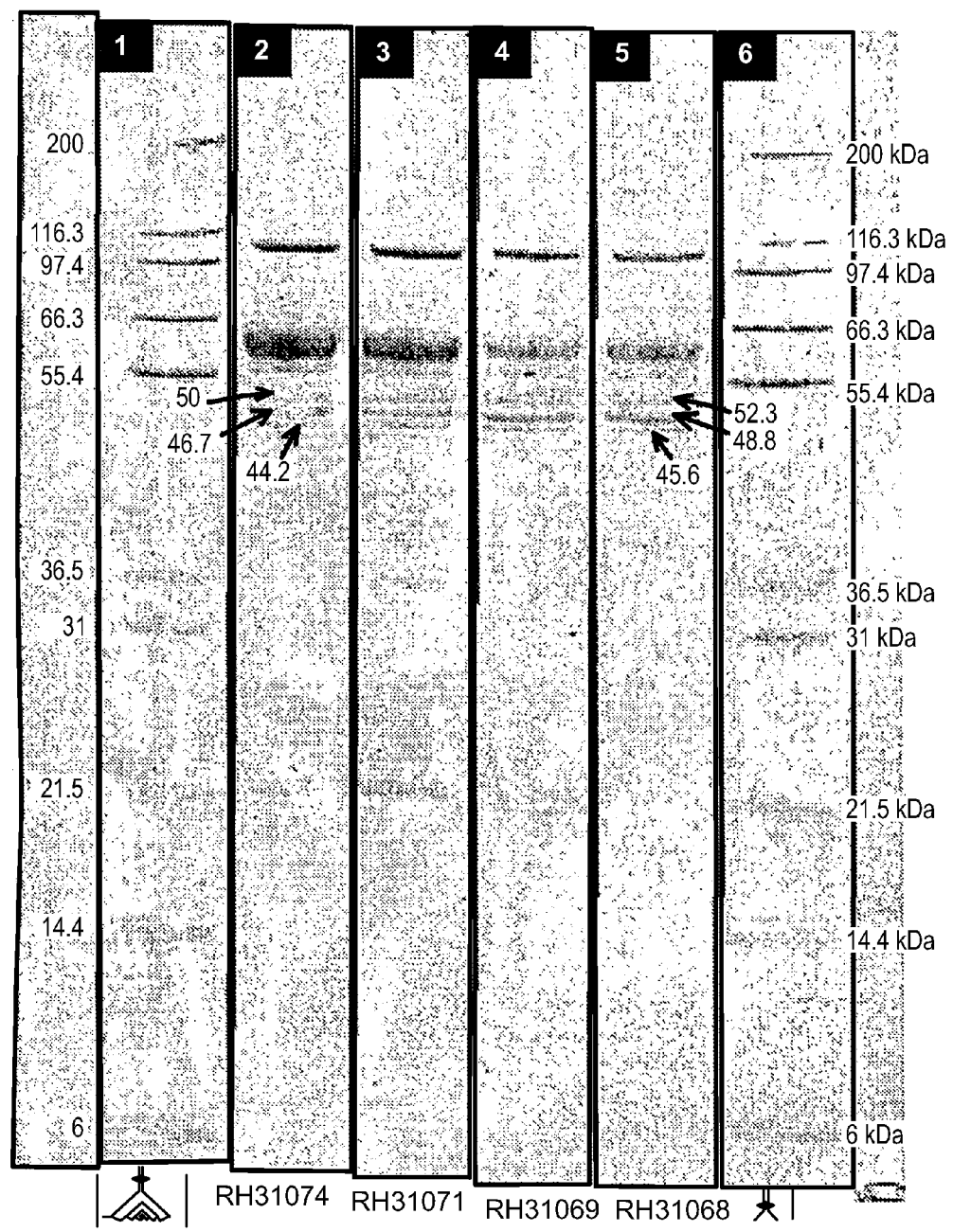

```
   1 cagagtgagc cggagctgaa gctggaaagt gtggtgattg tcagtcgtca
  51 tggtgtgcgt gctccaacca agccacgca actgatgcag gatgtcaccc
 101 cagacgcatg gccaacctgg ccgtaaaac tgggttggct gacaccgcgg
 151 ggtggtgagc taatcgccta tctcggacat taccaacgcc agcgtctggt
 201 agccgacgga ttgctggcga aaaagggctg cccgcagtct ggtcaggtcg
 251 cgattattgc tgatgtcgac gagcgtaccc gtaaaacagg cgaagccttc
 301 gccgcgggc tggcacctga ctgtgcaata accgtacata cccaggcaga
 351 tacgtccagt cccgatccgt tatttaatcc tctaaaaact ggcgtttgcc
 401 aactgataa cgcgaacgtg actgacgcga tcctcagcag ggcaggaggg
 451 tcaattgctg actttaccgg gcatcggcaa acggcgtttc gcgaactgga
 501 acggtgctt aattttccgc aatcaaactt gtgccttaaa cgtgagaaac
 551 aggacgaaag ctgttcatta acgcaggcat taccatcgga actcaaggtg
 601 agcgccgaca atgtctcatt aaccggtgcg gtaagcctcg catcaatgct
 651 gacggagata tttctcctgc aacaagcaca gggaatgccg gagccggggt
 701 gggaaggat caccgattca caccagtgga acacctgct aagtttgcat
 751 aacgcgcaat tttatttgct acaacgcacg ccagaggttg cccgcagccg
 801 cgccaccccg ttattagatt tgatcaagac agcgttgacg cccatccac
 851 cgcaaaaaca ggcgtatgt gtacattac ccacttcagt gctgtttatc
 901 gccggacacg atactaatct ggcaaatctc ggcggcgcac tggagctcaa
 951 ctggacgctt ccccgtcagc cggatcgg ctaaacac gccgccagtt ggtgaactgg
1001 tgtttgaacg ctggcgtcgg ctaagcgata acagccagtg gattcaggtt
1051 tcgctggtct tccagactt acagcagatg cgtgataaaa cgccgctgtc
1101 attaaatacg ccgcccgag agtgaaact gacctggca ggatgtgaag
1151 agcgaaatgc gcagggcatg tgttcgttgg caggtttac gcaaatcgtg
1201 aatgaagcac gcataccggc gtgcagtttg
```

FIG. 5

SEQUENCE LISTING

```
<160> NUMBER OF SEQ ID NOS: 8

<210> SEQ ID NO 1
<211> LENGTH: 1230
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1230)

<400> SEQUENCE: 1 cag agc gag ccc gag ctg aag ctg gag tcg gtc gtg atc gtc agc cgc       48
Gln Ser Glu Pro Glu Leu Lys Leu Glu Ser Val Val Ile Val Ser Arg
1               5                   10                  15 cac ggc gtg cgt gct cct acc aag gcc acg cag ctg atg cag gac gtc       96
His Gly Val Arg Ala Pro Thr Lys Ala Thr Gln Leu Met Gln Asp Val
                20                  25                  30 acc cct gac gcc tgg ccc acc tgg ccc gtc aag ctt ggc tgg ctg act      144
Thr Pro Asp Ala Trp Pro Thr Trp Pro Val Lys Leu Gly Trp Leu Thr
            35                  40                  45 cct cgc ggc ggt gag ctc atc gcc tac ctc gga cac tac caa cgc cag      192
Pro Arg Gly Gly Glu Leu Ile Ala Tyr Leu Gly His Tyr Gln Arg Gln
        50                  55                  60 cgt ctg gtt gcc gac gga ctc ctg gct aag aag gga tgc ccg cag tct      240
Arg Leu Val Ala Asp Gly Leu Leu Ala Lys Lys Gly Cys Pro Gln Ser
65                  70                  75                  80 ggc cag gtc gcg att atc gcc gat gtc gac gag cgt acc cgt aag acc      288
Gly Gln Val Ala Ile Ile Ala Asp Val Asp Glu Arg Thr Arg Lys Thr
                85                  90                  95 ggc gaa gcc ttc gct gcc ggc ctc gct cct gac tgt gcc atc acg gtc      336
Gly Glu Ala Phe Ala Ala Gly Leu Ala Pro Asp Cys Ala Ile Thr Val
```

```
            100                 105                 110
cac acc cag gca gac acg tcc agc ccc gat ccg ctg ttt aac cct ctc     384
His Thr Gln Ala Asp Thr Ser Ser Pro Asp Pro Leu Phe Asn Pro Leu
        115                 120                 125 aag act ggc gtc tgc caa ctg gat aac gcc aac gtg acc gac gcc atc     432
Lys Thr Gly Val Cys Gln Leu Asp Asn Ala Asn Val Thr Asp Ala Ile
130                 135                 140 ctc agc agg gct gga ggt tcc atc gcc gac ttc acc ggc cat cgg cag     480
Leu Ser Arg Ala Gly Gly Ser Ile Ala Asp Phe Thr Gly His Arg Gln
        145                 150                 155                 160 acg gcg ttc cgc gag ctg gag cgg gtc ctt aat ttt ccc cag tcg aac     528
Thr Ala Phe Arg Glu Leu Glu Arg Val Leu Asn Phe Pro Gln Ser Asn
                    165                 170                 175 ctg tgc ctc aag cgt gag aag cag gac gag agc tgt tcc ctg acc cag     576
Leu Cys Leu Lys Arg Glu Lys Gln Asp Glu Ser Cys Ser Leu Thr Gln
                180                 185                 190 gca ctc ccg tcg gaa ctc aag tac agc gcc gac aac gtc tcc ctt acc     624
Ala Leu Pro Ser Glu Leu Lys Tyr Ser Ala Asp Asn Val Ser Leu Thr
            195                 200                 205 ggt gcc gtt agc ctc gct tcc atg ctg acg gag atc ttc ctc ctg cag     672
Gly Ala Val Ser Leu Ala Ser Met Leu Thr Glu Ile Phe Leu Leu Gln
210                 215                 220 caa gcg cag gga atg ccc gag cct ggg tgg ggc cgc att acc gat tct     720
Gln Ala Gln Gly Met Pro Glu Pro Gly Trp Gly Arg Ile Thr Asp Ser
225                 230                 235                 240 cac cag tgg aac acc ctg ctc tcg ctt cac aac gcc cag ttc tat ctg     768
His Gln Trp Asn Thr Leu Leu Ser Leu His Asn Ala Gln Phe Tyr Leu
                    245                 250                 255 ctc caa cgc acg ccc gag gtt gcc cgc agc cgc gcc acc ccg ctg ctc     816
Leu Gln Arg Thr Pro Glu Val Ala Arg Ser Arg Ala Thr Pro Leu Leu
                260                 265                 270 gac ctc atc aag act gcg ctg acg ccc cac cct ccg cag aag cag gct     864
Asp Leu Ile Lys Thr Ala Leu Thr Pro His Pro Pro Gln Lys Gln Ala
            275                 280                 285 tac ggt gtc acc ctc ccc act tcc gtc ctg ttt atc gcc ggt cac gac     912
Tyr Gly Val Thr Leu Pro Thr Ser Val Leu Phe Ile Ala Gly His Asp
290                 295                 300 acc aac ctg gcc aat ctc ggc ggc gct ctg gag ctc aac tgg acg ctt     960
Thr Asn Leu Ala Asn Leu Gly Gly Ala Leu Glu Leu Asn Trp Thr Leu
305                 310                 315                 320 ccc gga cag ccg gat aac act ccc cct ggc ggt gag ctg gtg ttc gaa    1008
Pro Gly Gln Pro Asp Asn Thr Pro Pro Gly Gly Glu Leu Val Phe Glu
                    325                 330                 335 cgc tgg cgt cgg ctc agc gac aac tcc cag tgg att cag gtt tcg ctg    1056
Arg Trp Arg Arg Leu Ser Asp Asn Ser Gln Trp Ile Gln Val Ser Leu
                340                 345                 350 gtc ttc cag acc ctg cag cag atg cgc gac aaa acg ccc ctg tcc ctc    1104
Val Phe Gln Thr Leu Gln Gln Met Arg Asp Lys Thr Pro Leu Ser Leu
            355                 360                 365 aat acc cct ccc ggc gag gtc aag ctg acc ctg gca ggc tgt gaa gag    1152
Asn Thr Pro Pro Gly Glu Val Lys Leu Thr Leu Ala Gly Cys Glu Glu
370                 375                 380 cgc aac gcc cag ggc atg tgc tct ctc gct ggc ttt acg caa atc gtg    1200
Arg Asn Ala Gln Gly Met Cys Ser Leu Ala Gly Phe Thr Gln Ile Val
385                 390                 395                 400 aac gag gcc cgc atc ccc gct tgc tct ctg                            1230
Asn Glu Ala Arg Ile Pro Ala Cys Ser Leu
                405                 410

<210> SEQ ID NO 2
```

<211> LENGTH: 410
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

```
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Tyr Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gly Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
    370                 375                 380
```

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 3
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(54)

<400> SEQUENCE: 3 atg ggc gtc tct gct gtt cta ctt cct ttg tat ctc ctg tct gga gtc        48
Met Gly Val Ser Ala Val Leu Leu Pro Leu Tyr Leu Leu Ser Gly Val
1               5                   10                  15 acc tcc                                                                54
Thr Ser <210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Met Gly Val Ser Ala Val Leu Leu Pro Leu Tyr Leu Leu Ser Gly Val
1               5                   10                  15

Thr Ser

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ccgcggactg cgcatcatg                                                   19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ccgcggacta ggcatcatg                                                   19

<210> SEQ ID NO 7
<211> LENGTH: 1230
<212> TYPE: DNA
<213> ORGANISM: Escherichia coli
<220> FEATURE:
<221> NAME/KEY: CDS
<222> LOCATION: (1)..(1230)

<400> SEQUENCE: 7

```
cag agt gag ccg gag ctg aag ctg gaa agt gtg gtg att gtc agt cgt     48
Gln Ser Glu Pro Glu Leu Lys Leu Glu Ser Val Val Ile Val Ser Arg
1               5                   10                  15 cat ggt gtg cgt gct cca acc aag gcc acg caa ctg atg cag gat gtc    96
His Gly Val Arg Ala Pro Thr Lys Ala Thr Gln Leu Met Gln Asp Val
            20                  25                  30 acc cca gac gca tgg cca acc tgg ccg gta aaa ctg ggt tgg ctg aca   144
Thr Pro Asp Ala Trp Pro Thr Trp Pro Val Lys Leu Gly Trp Leu Thr
        35                  40                  45 ccg cgg ggt ggt gag cta atc gcc tat ctc gga cat tac caa cgc cag   192
Pro Arg Gly Gly Glu Leu Ile Ala Tyr Leu Gly His Tyr Gln Arg Gln
    50                  55                  60 cgt ctg gta gcc gac gga ttg ctg gcg aaa aag ggc tgc ccg cag tct   240
Arg Leu Val Ala Asp Gly Leu Leu Ala Lys Lys Gly Cys Pro Gln Ser
65                  70                  75                  80 ggt cag gtc gcg att att gct gat gtc gac gag cgt acc cgt aaa aca   288
Gly Gln Val Ala Ile Ile Ala Asp Val Asp Glu Arg Thr Arg Lys Thr
                85                  90                  95 ggc gaa gcc ttc gcc gcc ggg ctg gca cct gac tgt gca ata acc gta   336
Gly Glu Ala Phe Ala Ala Gly Leu Ala Pro Asp Cys Ala Ile Thr Val
            100                 105                 110 cat acc cag gca gat acg tcc agt ccc gat ccg tta ttt aat cct cta   384
His Thr Gln Ala Asp Thr Ser Ser Pro Asp Pro Leu Phe Asn Pro Leu
        115                 120                 125 aaa act ggc gtt tgc caa ctg gat aac gcg aac gtg act gac gcg atc   432
Lys Thr Gly Val Cys Gln Leu Asp Asn Ala Asn Val Thr Asp Ala Ile
    130                 135                 140 ctc agc agg gca gga ggg tca att gct gac ttt acc ggg cat cgg caa   480
Leu Ser Arg Ala Gly Gly Ser Ile Ala Asp Phe Thr Gly His Arg Gln
145                 150                 155                 160 acg gcg ttt cgc gaa ctg gaa cgg gtg ctt aat ttt ccg caa tca aac   528
Thr Ala Phe Arg Glu Leu Glu Arg Val Leu Asn Phe Pro Gln Ser Asn
                165                 170                 175 ttg tgc ctt aaa cgt gag aaa cag gac gaa agc tgt tca tta acg cag   576
Leu Cys Leu Lys Arg Glu Lys Gln Asp Glu Ser Cys Ser Leu Thr Gln
            180                 185                 190 gca tta cca tcg gaa ctc aag gtg agc gcc gac aat gtc tca tta acc   624
Ala Leu Pro Ser Glu Leu Lys Val Ser Ala Asp Asn Val Ser Leu Thr
        195                 200                 205 ggt gcg gta agc ctc gca tca atg ctg acg gag ata ttt ctc ctg caa   672
Gly Ala Val Ser Leu Ala Ser Met Leu Thr Glu Ile Phe Leu Leu Gln
    210                 215                 220 caa gca cag gga atg ccg gag ccg ggg tgg gga agg atc acc gat tca   720
Gln Ala Gln Gly Met Pro Glu Pro Gly Trp Gly Arg Ile Thr Asp Ser
225                 230                 235                 240 cac cag tgg aac acc ttg cta agt ttg cat aac gcg caa ttt tat ttg   768
His Gln Trp Asn Thr Leu Leu Ser Leu His Asn Ala Gln Phe Tyr Leu
                245                 250                 255 cta caa cgc acg cca gag gtt gcc cgc agc cgc gcc acc ccg tta tta   816
Leu Gln Arg Thr Pro Glu Val Ala Arg Ser Arg Ala Thr Pro Leu Leu
            260                 265                 270 gat ttg atc aag aca gcg ttg acg ccc cat cca ccg caa aaa cag gcg   864
Asp Leu Ile Lys Thr Ala Leu Thr Pro His Pro Pro Gln Lys Gln Ala
        275                 280                 285 tat ggt gtg aca tta ccc act tca gtg ctg ttt atc gcc gga cac gat   912
Tyr Gly Val Thr Leu Pro Thr Ser Val Leu Phe Ile Ala Gly His Asp
    290                 295                 300 act aat ctg gca aat ctc ggc ggc gca ctg gag ctc aac tgg acg ctt   960
Thr Asn Leu Ala Asn Leu Gly Gly Ala Leu Glu Leu Asn Trp Thr Leu
305                 310                 315                 320
```

-continued

```
ccc ggt cag ccg gat aac acg ccg cca ggt ggt gaa ctg gtg ttt gaa      1008
Pro Gly Gln Pro Asp Asn Thr Pro Pro Gly Gly Glu Leu Val Phe Glu
            325                 330                 335 cgc tgg cgt cgg cta agc gat aac agc cag tgg att cag gtt tcg ctg      1056
Arg Trp Arg Arg Leu Ser Asp Asn Ser Gln Trp Ile Gln Val Ser Leu
            340                 345                 350 gtc ttc cag act tta cag cag atg cgt gat aaa acg ccg ctg tca tta      1104
Val Phe Gln Thr Leu Gln Gln Met Arg Asp Lys Thr Pro Leu Ser Leu
            355                 360                 365 aat acg ccg ccc gga gag gtg aaa ctg acc ctg gca gga tgt gaa gag      1152
Asn Thr Pro Pro Gly Glu Val Lys Leu Thr Leu Ala Gly Cys Glu Glu
370                 375                 380 cga aat gcg cag ggc atg tgt tcg ttg gca ggt ttt acg caa atc gtg      1200
Arg Asn Ala Gln Gly Met Cys Ser Leu Ala Gly Phe Thr Gln Ile Val
385                 390                 395                 400 aat gaa gca cgc ata ccg gcg tgc agt ttg                              1230
Asn Glu Ala Arg Ile Pro Ala Cys Ser Leu
            405                 410

<210> SEQ ID NO 8
<211> LENGTH: 410
<212> TYPE: PRT
<213> ORGANISM: Escherichia coli

<400> SEQUENCE: 8

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
    130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255
```

```
Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
            275                 280                 285

Tyr Gly Val Thr Leu Pro Thr Ser Val Leu Phe Ile Ala Gly His Asp
            290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
        370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410
```

POLYPEPTIDE HAVING PHYTASE ACTIVITY AND NUCLEOTIDE SEQUENCE ENCODING THE SAME

This application is a Continuation of PCT/EP2005/011108, filed Oct. 14, 2005, which claimed the prior benefit of DE 10 2004 050 410.5, filed Oct. 15, 2004.

The present invention relates to a recombinant DNA molecule encoding a polypeptide having phytase activity, and the encoded polypeptide as such. Specifically, the invention relates to a recombinant DNA molecule encoding a polypeptide having phytase activity, wherein the DNA sequence has been obtained by a variation of the mature wild-type *E. coli* phytase, wherein the defined amino acid positions are modified as compared to the wild-type sequence. Furthermore, the invention relates to a method for expressing the recombinant phytase as well as its use in food and feed technology.

Phytic acid or myoinositol-1,2,3,4,5,6-hexakisdihydrogenphosphate (abbreviated as myoinositol hexakisphosphate) is the main source of inositol and the primary storage form of phosphate in plant seed. In the seed of legumes approximately 70% of the phosphate content is present as a mixed potassium, magnesium and calcium salt of phytic acid. Seed, cereal grains and legumes are important components of food and feed preparations, in particular of animal feed preparations; but cereals and legumes also gain increasing importance in human nutrition.

The phosphate units of phytic acid bind as a complex bivalent and trivalent cations such as metal ions, i.e. nutrition-physiologically important ions such as calcium, ion, zinc and magnesium as well as the trace elements manganese, copper and molybdenum. Apart from this phytic acid also binds proteins by electrostatic interaction to a certain extent.

Phytic acid and its salts, the phytates, are often not metabolised as they cannot be absorbed from the gastrointestinal tract, i.e. neither the phosphors contained therein nor the chelated metal ions nor the bound proteins are nutrition-physiologically available.

As phosphor is an essential element for the growth of all organisms, food and feed have to be supplemented with inorganic phosphate. The nutrition-physiologically essential ions such as iron and calcium have very often to be supplemented as well. Moreover, the nutrition-physiological value of any diet is reduced as proteins are bound by phytic acid. Consequently, phytic acid is often denoted as a factor contrary to the nutritional value ("Anti-Nährwertfaktor").

Furthermore, the phosphors of the phytate are excreted via the gastro-intestinal tract of the animals due to a lack of metabolism, which leads to undesired phosphate pollution of the environment, which can, for example, lead to eutrophication of waters and to excessive growth of algae.

Phytic acid or phytates (in the following these terms are used synonymously except otherwise indicated) can be degraded by phytases. Phytic acid containing plant seed contain endogenous phytase enzymes. Upon their intake the phytates in food and feed are theoretically hydrolysable by the endogenous plant phytases, by phytases from the intestinal flora and by phytases from the intestinal mucosa. In practice, however, the hydrolyse potential of the endogenous plant phytases and of the phytases occurring in the intestinum, if present, is by far not sufficient for ensuring significantly the bio-availability of the phosphorous bound in the phytates. Thus, exogenous phytases are frequently added to food and feed.

Phytases can be produced by plants as well as by microorganisms. Among the micro-organisms, phytase producing bacteria as well as phytase producing fungi and yeasts are known.

The naturally occurring phytase producers have, however, the disadvantage that the phytase is only formed in certain amounts and with defined properties. As explained above, there is, however, an increased need for phytase, specifically for food and feed industry.

An object of the present invention is thus to provide a polypeptide having phytase activity, which can be produced economically. Specifically, it shall be possible to produce the phytase cost-effectively. The phytase shall further maintain the essential properties of the natural *E. coli* wild-type phytase, but shall distinguish itself by an increased activity in the culture supernatant and an improved secretability, respectively. Specifically, the ability to ameliorate the availability of phosphate in vivo and in vitro as well as the suitability of a baking aid count among the essential properties of the natural wild-type phytase.

A further object of the present invention is to provide a gene for a polypeptide having phytase activity, which, upon expression in a host cell, results in an increased activity of the so encoded protein in the culture supernatant and an increased secretion of the polypeptide, respectively. It shall be possible to produce the polypeptide economically and cost-effectively. Specifically, the expression of the polypeptide shall result in increased yields in eukaryotic microorganisms compared to the expression of the wild-type phytase. Furthermore, the DNA sequences encoding the polypeptide, corresponding DNA constructs and vectors as well as a source for the recombinant enzyme being suitable for the commercial use for food and feed and in industrial processes, and compositions containing the enzyme according to the invention shall be provided.

It has now surprisingly been found that a mutation in the region of inclusive amino acid 189 to inclusive 211 and/or of amino acid inclusive position 137 to inclusive 152 of the wild-type phytase of *E. coli* results in an increased activity in the whole culture supernatant by the protein phytase without affecting the beneficial effects and essential properties of the wild-type *E. coli* phytase.

Several phytases from *E. coli* are disclosed in literature, e.g. in Dassa et al., 1990, J. Bacteriol. 172:5497-5500. Genetically modified mutants of the *E. coli* phytase resulting in an increased thermal stability and/or higher specific activities have also been disclosed (Rodriguez et al., 2000, Arch. Biochem. Biophys., 382: 105-112, Lanahan et al., 2003, US patent application 2003 0157646 A1, WO 01/90333). A site-specific mutagenesis of *Escherichia coli* phytase with improved enzymatic properties is further disclosed in WO 01/36607. However, the Val-Tyr mutant at position 200 disclosed herein does not correspond to the mutation at position 200 according to the invention, as another way of counting the sequence has been used according to WO 01/36607, i.e. the leader sequence has been included in the counting. Thus, position 222 in the sequence according to said publication (WO 01/36607) corresponds to position 200 of the counting according to the invention. Further proteins having phytase activity are disclosed in WO 99/08539, WO 01/90333, WO 02/095003, WO 03/038035, WO 03/038111, WO 04/015084 and WO 00/71728.

Moreover, the publication Garrett et al., Applied Environ. Microbiol., 2004, 70 (5), 3041-3046 discloses mutants of the *E. coli* phytase having increased thermal and gastrointestinal stability.

However, the prior art does not contain a description of mutations in the *E. coli* phytase resulting in an increased production of a prokaryotic enzyme upon expression by an eukaryotic micro-organism. Moreover, the prior art does not contain indications as to achieve an increased activity of the thus produced enzyme in the culture supernatant by a variation and specifically a mutation of the *E. coli* phytase. Specifically, the prior art does not contain an indication as to the functional significance of positions 198 to 211 and/or of positions 137 to 152 of the wild-type *E. coli* phytase sequence. Most particularly, the prior art does not contain an indication as to the functional significance of position 200 of the wild-type *E. coli* phytase sequence.

This object is solved by a recombinant DNA molecule, which, upon expression in a prokaryotic or eukaryotic host cell, encodes a polypeptide having phytase activity, wherein the recombinant DNA molecule comprises a DNA sequence selected from a) DNA sequences which have been obtained by variations of the mature wild-type *E. coli* phytase sequence, wherein at least one amino acid in the region of position 189 to 211 and/or an amino acid in the region of position 137 to 152 is mutated as compared to the wild-type sequence, b) DNA sequences having a homology of 70% to 100% to the sequences according to a), c) DNA sequences which are related to the sequences according to a) and b) due to the degeneracy of the genetic code, wherein the recombinant DNA molecule is, upon expression in a suitable host cell, associated with an increased activity of the thus encoded protein in the culture supernatant, as well as by a polypeptide having phytase activity and being encoded by one of said recombinant DNA molecules.

The invention relates further to a method for producing a polypeptide having phytase activity according to recombinant techniques, comprising growing recombinant prokaryotic and/or eukaryotic host cells, which contain a nucleic acid sequence according to the invention, under conditions conductive to the expression of the enzyme as well as the subsequent recovery of the enzyme. The invention furthermore relates to the use of said polypeptide having phytase activity in conventional methods, e.g., in methods releasing minerals from phytate complexes in plant materials either in vitro, e.g., in is the treatment of feed, or its use in baking or in vivo, i.e. the administration of the polypeptide having phytase activity to animals. Moreover, the invention relates to the use of the polynucleotide sequences according to the invention for producing probes for finding similar sequences, which encode corresponding enzymes, in other organisms as well as for transforming host cells.

Moreover, the invention relates to a signal sequence derived from the gene of *Aspergillus niger* phytase.

The enclosed figures illustrate the invention in more detail:

FIG. 1: SDS-PAGE of culture supernatants of strains transformed with the plasmids pKDa2 and pKDa4. Lanes 1 and 6 contain marker proteins. The specific description is contained in example 6 and table 3.

Figure 2:
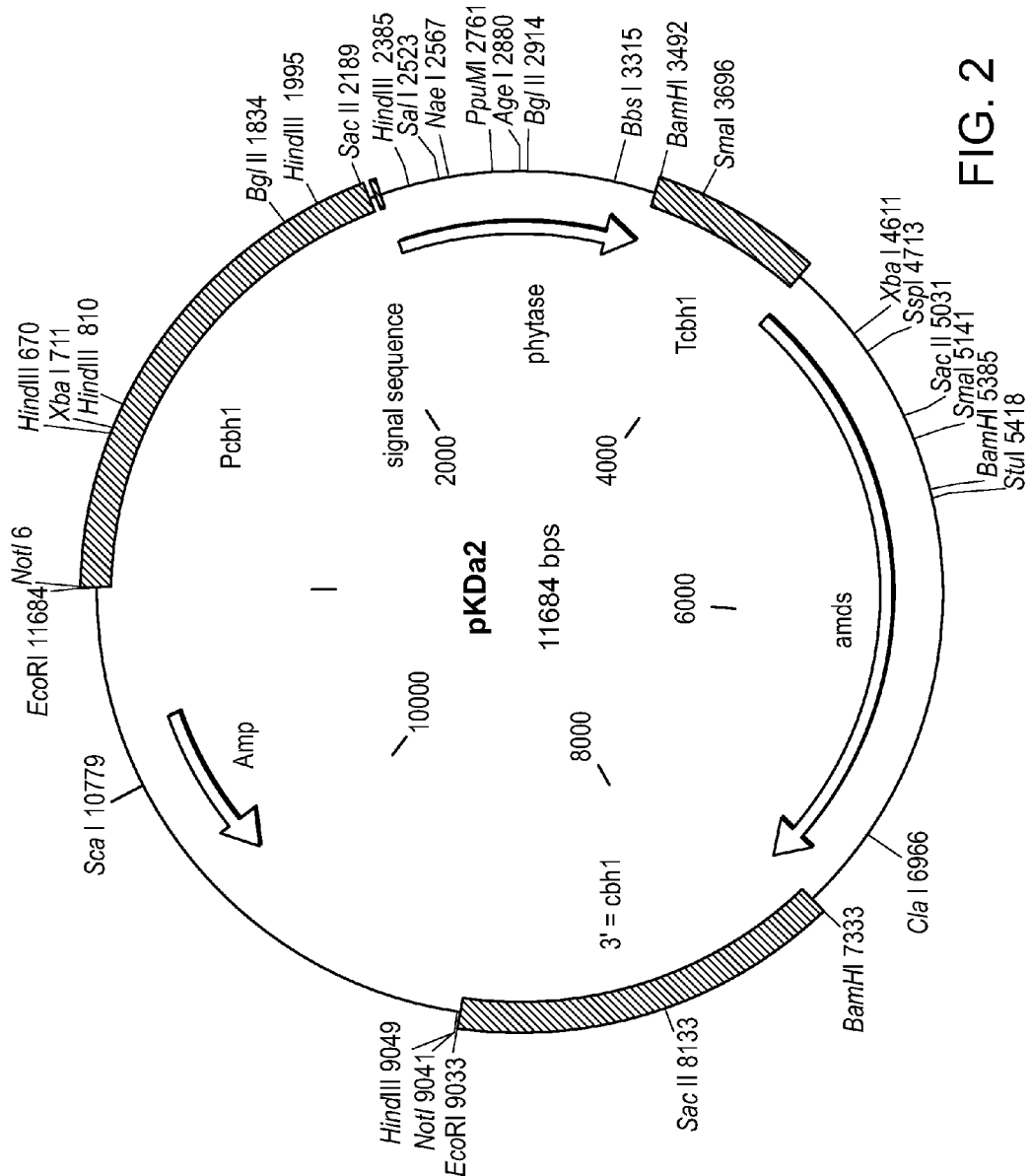

FIG. 2: Plasmid map of pKDa2 (Tyr$^{200}$ mutant)

Figure 3:
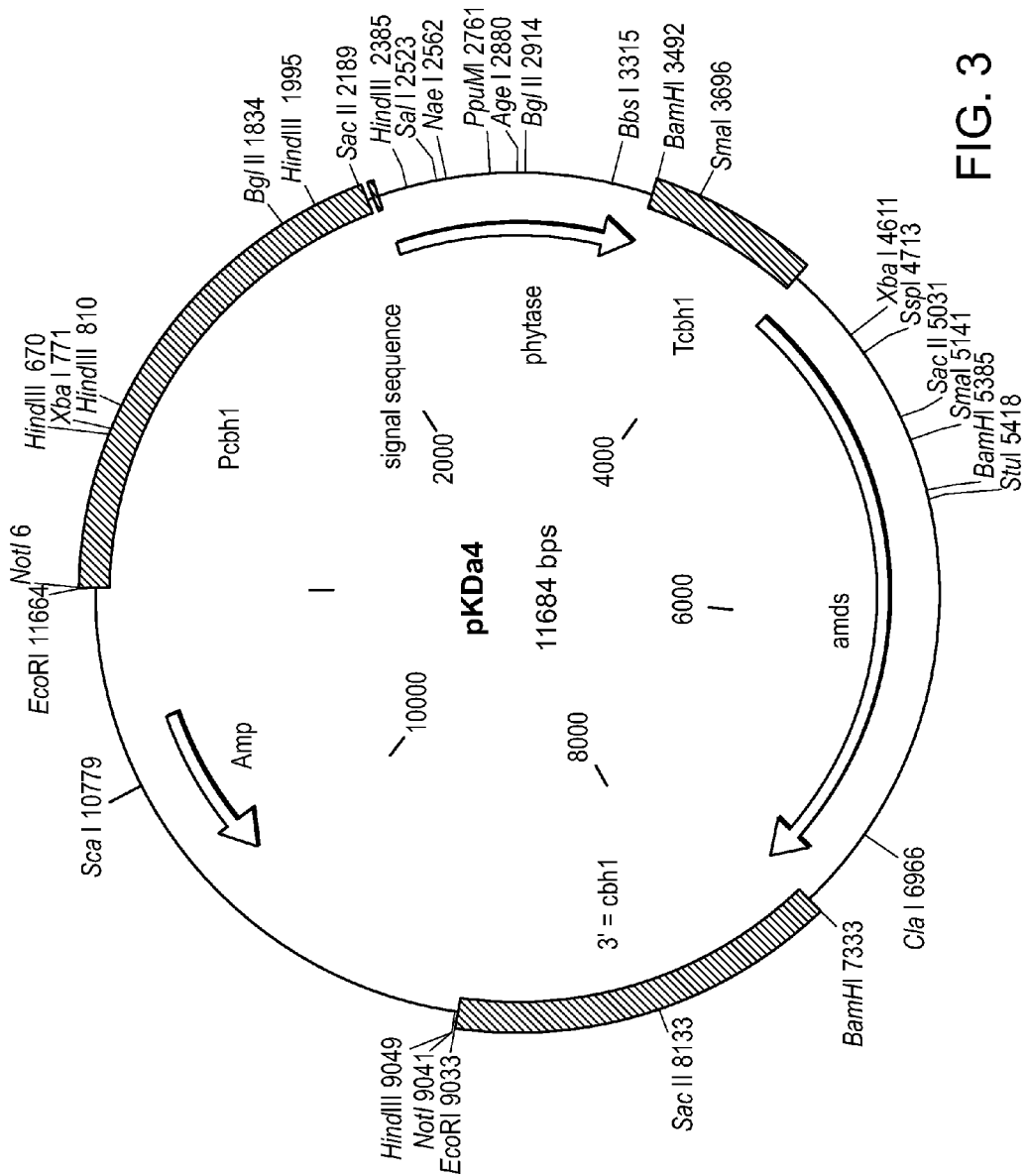

FIG. 3: Plasmid map of pKDa4 (wild-type)

Figure 4:
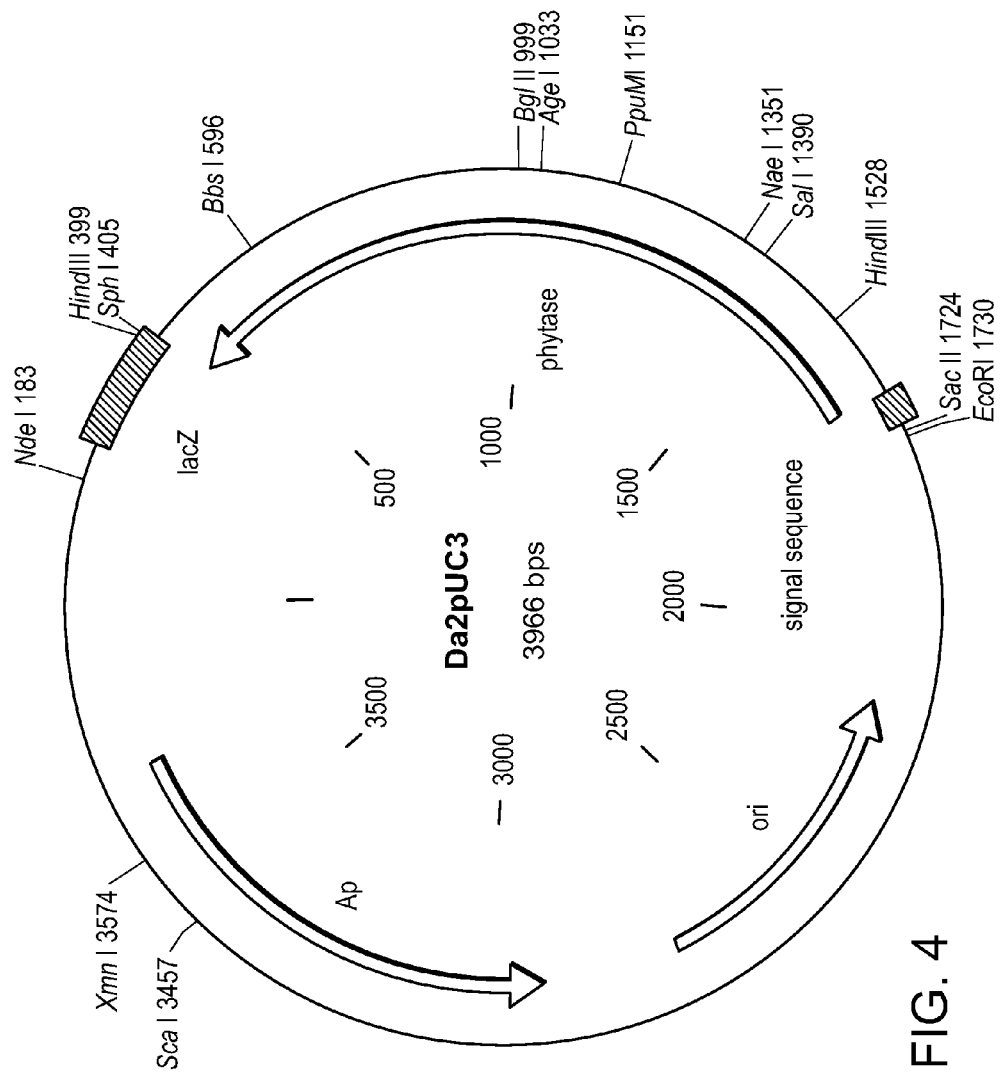

FIG. 4: Plasmid map of Da2pUC3

FIG. 5: DNA sequence (SEQ ID NO: 7) encoding the *E. coli* wild-type phytase (SEQ ID NO: 8) (*E. coli* codon usage) Dassa et al., 1990, J. Bacteriol. 172: 5497-5500, mature protein.

The plasmid Da2pUC3 has been deposited under accession number DSM 16396 on May 7, 2004 at the Deutschen Sammlung von Mikroorganismen und Zellkulturen GmbH (DSMZ), Mascheroder Weg 1b, D-38124 Braunschweig according to the provisions of the Budapest Treaty.

It has surprisingly been found that amino acid mutation in the region of position 198 to 211 (including the limit values) and/or an amino acid mutation in the region of position 137 to 152 (including the limit values) of the wild-type phytase sequence of *E. coli* is associated with a significantly increased activity in the culture supernatant upon expression in a host cell. Preferably, at least one amino acid in the region of position 197 to 209 (including the limit values) and/or an amino acid in the region of position 137 to 152 (including the limit values) is mutated as compared to the wild-type sequence. More preferably, at least one amino acid at position 198, 200, 205 and 207 and/or at position 144, 145 and 152 is mutated. Preferred mutations in the region of position 189 to 211 are Val 200→Leu, Val 200→Ile, Val 200→Pro, Val 200→Tyr, Leu 198→Ile, Val 205→Leu, Val 205→Ile, Leu 207→Tyr, Leu 207→Phe and in the region of position 137 to 152 Ile 144→Tyr, Leu 145→Ile, Ile 152→Phe. Further preferred mutations are Val 200→Leu, Val 200→Pro, Val 200→Tyr and Ile 144→Tyr. It is especially preferred that a mutation is present at position Val 200. This amino acid is preferably substituted by an aromatic amino acid such as tyrosin, by a hydrophobic amino acid such as leucin or isoleucin or by prolin. Preferably, the mutation at position 200 is Tyr. Moreover, also double mutants can be generated with the proviso that mutation Ile 144→Tyr is not associated with a mutation of Val 200, as well with the further proviso that mutation Ile 152→Phe is not combined with any mutation of Leu 207. A preferred double mutant is Leu 198→Ile in combination with Leu 145→Ile. Without being bound by the following theoretical explanation, it is expected that alterations in two spacially adjacent structure regions of the phytase, i.e. the β-sheet and the α-helix result from the modification according to the invention, and that these regions are thus altered by hydrophobic interaction, so as to result in a better packing density. The packing density in turn results in an increased activity in the culture supernatant and secretion of a thus modified enzyme, respectively. Within the scope of the above proviso, any mutations can be made and combined in said regions as long as a micro-organism transformed with a corresponding DNA sequence secretes from the cell the encoded phytase in increased amounts and, respectively, with the property of resulting in increased activity (total activity) in the culture supernatant, wherein the enzymatic activity and the further physiological properties of the wild-type *E. coli* phytase are maintained. Preferably the improvement of the activity in the culture supernatant and of the secretion efficiency of a mutant, respectively, is by at least 10%, more preferred at least 20%, as compared to the wild-type *E. coli* phytase upon measurement under identical conditions. The determination of the enzymatic activity of the phytase and the measurement of further physiological properties of the phytase can be carried out according to methods known per se.

The achievement of an augmentation of the activity in the culture supernatant and of the secretion efficiency of the phytase, respectively, by at least 10% as compared to the secretion efficiency of the wild-type phytase was surprising and has not been obvious. It was in particular surprising that the mutant Val 200→Tyr is associated with an augmentation of the secretion efficiency by 100% as compared to the wild-type phytase (cf. example 4).

Attempts to improve the properties of phytase are reported in the prior art. Thus, the publication Archives Biochem. Biophys., 2000, 382 (1), 105-122 describes the activities of phytase in the culture supernatant upon secretion by the yeast *Pichia pastoris* on page 109, table 3. The wild-type *E. coli* phytase (which is not precisely sequence-identical to the sequence pKDa4 according to the invention) was secreted at 117 units ml$^{-1}$ after 96 hours. It is to be noted that the determination of the activity according to said publication is not identical to the determination of the activity according to example 4 of the present invention. According to the prior art in the publication mentioned above, the substrate is incubated with the enzyme at pH 2.5. According to the invention, the incubation is carried out at pH 5.0. As can be taken from the curves on page 109, FIG. 3 of the publication, 117 U ml$^{-1}$ at pH 2.5 would correspond to only approximately 60 U ml$^{-1}$ at pH 5 (52% residual activity). Thus, the enzymatic activity of the secreted *E. coli* wild-type phytase, encoded by the *E. coli* wild-type codon usage, in said publication is substantially less than the secreted enzyme activity of 158 to 188 U ml$^{-1}$ obtained with the pKDa4 transformed *T. reesei* strain.

The DNA sequence corresponding to the phytase sequence mutated according to the invention can be realised using any codon usage as far as the secretion level is not adversely affected by the codon usage. Thus, for example, the codon usage of the micro-organism used for expression can be used but also the *E. coli* codon usage and a variation thereof, respectively, can be used. Moreover, the mutated *E. coli* phytase sequence according to the invention can contain further sequence variations. Thereby, any variations can be made in addition to the mutations described above, as long as the property of achieving a higher activity in the culture supernatant and secretion efficiency, respectively, is not adversely affected and as long as the enzymatic activity and further essential properties of the *E. coli* wild-type phytase are maintained.

Corresponding variations are well known to a person skilled in the art of recombinant DNA and comprise the above mutations as well as the exemplary variations set forth below.

According to the invention, addition and/or deletion molecules of the polypeptide modified according to the invention can be used. Thus, the polypeptide modified according to the invention having a phytase activity can be elongated by adding further sequences at the N-terminal and/or C-terminal ends. Thereby, hybrid molecules can be created, which have further advantageous properties. For example, fusion proteins and proteins being natively secreted in high amounts, respectively, can be added, whereby the secretion efficiency is further improved. Moreover, active sequence segments of other enzymes can be added for obtaining enzymes having multiple specifity. Moreover, polar and non-polar sequences can be added for specifically influencing the solubility properties and the capability to pass the membrane ("Membrangängigkeit"), respectively, of the thus obtained enzyme. Preferably, the N-terminal end is linked to an *Aspergillus* phytase or an acid phosphatase. Elongations of the C-terminus of the mutated *E. coli* phytase sequence can be made in the same manner. Thereby, phytases having an altered quaternary structure can be obtained.

According to the invention, also sequence segments of the polypeptide having phytase activity can be deleted as long as the property of the increased secretion and activity in the culture supernatant, respectively, wherein the phytase activity is maintained, is not affected.

The mutations, elongations and truncations can be carried out by methods known per se in the prior art.

The modifications of the polypeptide having phytase activity taken into consideration above correspond to respective mutations and modifications, respectively, of the corresponding DNA molecule. According to the invention, also such sequences hybridising under relaxed or stringent conditions with the sequences according to the invention are taken into consideration. Moreover, the invention also relates to such sequences exhibiting a homology of at least 70%, more preferred of at least 90% and in particular at least 95% to the claimed nucleotide sequence and the claimed parts thereof, respectively, as long as the respective sequences result in an increase of the activity in the culture supernatant and the secretion efficiency, respectively, of the polypeptide having phytase activity encoded by them. Preferably, the homology is from 70 to 100 percent. The degree of identity is thereby preferably determined, so that the number of residues of the shorter sequence participating in the comparison and having a "corresponding" counterpart in the other sequence is determined. For the purpose of the present invention, the homology is thereby preferably determined as usual using the usual algorithms. According to the invention, only the cDNAs of the respective mature proteins are taken into account for comparison. Similarly, preferably identical sequence counterparts were determined according to the invention as homologous sequences using known computer programs. An example for such a program is the program Clone Manager Suite containing the program part Align Plus and being distributed by Scientific & Educational Software, Durham, N.C., USA. Thereby, a comparison of two DNA sequences as defined above is carried out using the option local alignment either according to the method FastScan—MaxScore or according to the method Needleman-Wunsch and by retaining the default values. Specifically, the program version "Clone Manager 7 Align Plus 5" with the functions "Compare Two Sequences/Local Fast Scan-Max Score/Compare DNA sequences" has been applied according to the invention for calculating the homology. Thereby, the algorithms accessible from the following sources have been used: Hirschberg, D. S. 1975. A linear space algorithm for computing longest common subsequences. Commun Assoc Comput Mach 18: 341-343; Myers, E. W. and W. Miller. 1988. Optimal alignments in linear space. CABIOS 4:1, 11-17; Chao, K-M, W. R. Pearson and W. Miller. 1992. Aligning two sequences within a specified diagonal band. CABIOS 8:5, 481-487. The invention relates furthermore also to DNA sequences that are related to the sequences according to the invention due to the degeneracy of the genetic code as well as allelic variants thereof. The degeneracy of the genetic code can thereby results due to natural degeneracy or due to a specifically selected codon usage. Naturally occurring allelic variants can be identified using well-known techniques of molecular biology, such as the polymerase chain reaction (PCR) and hybridisation techniques.

A DNA sequence encoding a polypeptide according to the invention can be used for transforming any host cells such as cells of fungi, yeasts, bacteria, plants or mammals. Thus transformed cells distinguish themselves by an increased secretion of phytase. The thus produced phytase enzyme also results in an efficient phosphate release from myoinositol phosphates.

The terms protein, peptide and polypeptide are to be used interchangeably. A polypeptide or enzyme having phytase activity or a phytase shall designate any enzyme being able to cause the release of inorganic phosphate from various myoinositol phosphates. Examples for such myoinositol phosphate (phytase) substrates are phytic acid and any salts thereof, for example, sodium phytate or potassium phytate or mixed salts. Any positional isomers of the di-, tri-, tetra- or pentaphosphates of myoinositol can also serve as phytase substrate. The phytase activity can be determined using any assay wherein one of said substrates is used. The phytase variant according to the invention comprises polypeptide variants that derive from a specific phytase by deletion or addition of one or more amino acids to the N-terminal and/or C-terminal end of the native protein, deletion or addition of one or more amino acids at one or more positions in the native protein, or substitution of one or more amino acids at one or more positions in the phytase. The generation of such variants is commonly known in the art. For example, amino acid sequence variants of the polypeptides can be made by mutation in the DNA. Methods for mutagenesis and nucleotide sequence alteration are well known in the art (see, for example, Kunkel, Proc. Natl. Acad. Sci. USA, 82:488 (1985), Kunkel et al., Methods in Enzymol., 154:367 (1987), U.S. Pat. No. 4,873,192, Walker and Gaastra, eds., Techniques in Molecular Biology, Mac Millan Publishing Company, New York (1983)). Indications on suitable amino acid substitutions, which do not affect the biological activity of the protein of interest, are found in the model of Dayhoff et al., Atlas of Protein Sequence and Structure, Natl. Biomed. Res. Found., Washington, D.C. (1987). Conservative substitution such as the exchange of one amino acid for another amino acid having similar properties are preferred.

The invention also relates to isolated or substantially purified nucleic acid or protein compositions. Therein, an isolated or purified polynucleotide/polypeptide and segment thereof, respectively, designates a polynucleotide and polypeptide and segment thereof, respectively, which is present in a form isolated from its native environment. An isolated polynucleic acid segment or polypeptide can be present in a purified form or can be present in a non-native environment, such as, for example, a transgenic host cell. For example, an isolated or purified polynucleotide segment or protein or a biologically active part thereof is essentially free of further cellular material or culture medium upon production according recombinant techniques or is essentially free of chemical precursors or other chemical compounds. Preferably, an isolated polynucleotide is free of sequences (preferably, protein-encoding sequences) naturally flanking the nucleic acid (i.e. sequences localised at the 5'- and 3'-ends of the nucleic acid) in the genomic DNA of the organism from which the nucleic acid is derived. According to different embodiments, the isolated nucleic acid molecule can, for example, contain less than approximately 5 kb, 4 kb, 3 kb, 2 kb, 1 kb, 0.5 kb or 0.1 kb of nucleotide sequences naturally flanking the nucleic acid molecule in the genomic DNA of the cell from which the nucleic acid derives. A protein that is essentially free of cellular material comprises compositions of protein or polypeptide having less than approximately 70%, 50%, 30%, 20%, 10%, 5% (on the basis of the dry weight) of contaminating protein. When the protein according to the invention or a biologically active fragment thereof is produced recombinantly, the culture medium preferably comprises less than approximately 70%, 50%, 30%, 20%, 10% or 5% (on the basis of the dry weight) of chemical precursors or non-proteinacious chemical substances. Fragments and variants of the nucleotide sequences according to the inventions or proteins or protein segments encoded by them are also within the scope of the invention. A fragment designates a part of the nucleotide sequence or a part of the amino acid sequence and thus a part of the polypeptide or protein, which is encoded by it.

The invention also relates to expression cassettes, which can be used for the transfer ("Einschleusung") of an open reading frame encoding a phytase according to the invention into a host cell. They preferably comprise a transcription initiation region, which is linked to the open reading frame. Such an expression cassette can contain a plurality of restriction sites for inserting the open reading frame and/or other DNAs, e.g. a transcription regulator region and/or selectable marker genes. The transcription cassette comprises in the 5' →3' direction of the transcription a transcription and translation initiation region, the DNA sequence of interest and a transcription and translation termination region, which is functional in a microbial cell. The termination region can be native vis-à-vis the transcription initiation region, can be native vis-à-vis the DNA sequence of interest or can derive from any other source.

The term "open reading frame" (ORF) designates the amino acid sequence that is encoded between the translation start and stop codons as a coding sequence. The terms "start codon" and "stop codon" designate a unit of three contiguous nucleotides (codons) in a coding sequence, which specifies the chain start and stop of the protein synthesis (mRNA translation).

"Operable Linkage" designates in connection with a nucleic acid a linkage as a part of the same nucleic acid molecule in a an appropriate positioning and orientation to the transcriptional start of the promoter. DNA operably linked to a promoter is under control of the transcription initiation regulation of the promoter. Coding sequences can be operably linked with the regulator sequence in sense or anti-sense orientation. With reference to polypeptides, operable linkage means the linkage as a part of the same polypeptide, i.e. via peptidyl bonds.

Any promoters can be used according to the invention. A promoter designates the nucleotide sequence, which is usually upstream (5') vis-à-vis the coding sequence, and controls the expression of the coding sequence by providing the recognition for the RNA polymerase and other factors, which are necessary for a correct transcription. The promoter used according to the invention can comprise a minimal promoter, i.e. a short DNA sequence of a TATA box and other sequences, which specify the transcription initiation site, which are attached to the regulator elements for controlling the expression.

The promoter according to the invention can also comprise a nucleotide sequence comprising a minimal promoter and regulator elements, which is able to control the expression of a coding sequence or a functional RNA. This type of promoter sequence consists of proximal and distal upstream elements, wherein the latter elements are often designated as enhancers. Consequently, an enhancer is a DNA sequence, which can stimulate the promoter activity and can be a intrinsic element of the promoter or an inserted heterologous element for increasing the expression level or tissue specifity of a promoter. It can work in both orientations and can even work upon a placing upstream or downstream of the promoter. Enhancers as well as other upstream promoter elements bind sequence-specific DNA-binding proteins, which mediate their effects. Promoters can be derived from a native gene in their entity or can be composed of different elements, which derive from different naturally occurring promoters or can even be composed of synthetic DNA segments. A promoter can also contain DNA sequences that are involved in the binding of protein factors controlling the efficiency of the transcription initiation as a response to physiological conditions or conditions attributable to the development.

Promoter elements, in particular TATA elements, which are inactive or have a strongly reduced promoter activity in the absence of an upstream activation are designated as minimal promoters or core promoters. In presence of an appropriate transcription factor or of appropriate transcription factors, respectively, the function of the minimal promoter results in allowing for the transcription. Thus, a minimal or core promoter only consists of all basic elements that are necessary for transcription initiation, e.g. a TATA box and/or an initiator.

The invention also relates to vectors containing DNA according to the invention. Said vectors comprise any plasmids, cosmids, phages and other vectors in double-stranded or single-stranded, linear or circular form, which can optionally be self-transmissible or mobilisable, and which can transform a prokaryotic or eukaryotic host either by integration into the cellular genome or which are extrachromosomal (e.g. autonomously replicating plasmids having an origin of replication).

Vectors, plasmids, cosmids, yeast artificial chromosomes (YACs), bacterial artificial chromosomes (BACs) and DNA segments for use for the transformation of cells generally comprise the phytase-encoding DNA according to the invention as well as an other DNA, such as cDNA, a gene ore genes, to be transferred or introduced, respectively, into the cells. Said DNA constructs can comprise further structures such as promoters, enhancers, polylinkers or also regulator genes, as necessary. One of the DNA segments or genes selected for cellular introduction conveniently encode(s) a protein that is expressed in the thus obtained transformed (recombinant) cells and which leads to a screenable or selectable trait and/or converse an improved phenotype to the transformed cell.

The construction of vectors that can be used according to the invention is known to a person skilled in the art having regard to the above disclosure (cf. e.g. Sambrook et al., Molecular Cloning: A Laboratory Manual ($2^{nd}$ edition, Coldspring Harbor Laboratory Press, Plainview, N.Y. (1989)). The expression cassette according to the invention can contain one or more restriction site(s) for placing the phytase-encoding nucleotide under regulation of a regulator sequence. The expression cassette can also contain a termination signal operably linked to the polynucleotide as well as regulator sequences, which are necessary for a correct translation of the polynucleotide. The expression cassette containing the polynucleotide according to the invention can be chimeric, i.e. at least on of its components is heterologous as regards at least one of the other components. The expression of the polynucleotide in the expression cassette can be under control of a constitutive promoter, an inducible promoter, a regulated promoter, a viral promoter or a synthetic promoter.

The vectors can already contain regulator elements, for example, promoters, or the DNA sequences according to the invention can be manipulated as to contain such elements. Suitable promoter elements which can be used are known in the art and are, for example, the cbh 1 or the cbh 2 promoter for *Trichoderma reesei*, the amy promoter for *Aspergillus oryzae*, the xyl, glaA, alcA, aphA, tpiA, gpdA, sucI and the pkiA promoter for *Aspergillus niger*. Suitable promoter elements, which can be used for expression in yeast, are known in the art and are, for example, the pho5 promoter or the gap promoter for expression in *Saccharomyces cerevisiae* and for *Pichia pastoris*, e.g. aoxI promoter or the fmd promoter or the mox promoter for *H. polymorpha*.

DNA suitable for introduction into cells can comprise DNA derived or isolated from any source apart from the DNA according to the invention. An example for a derived DNA is a DNA sequence that has been identified as a useful fragment in a given organism and which has then been chemically synthesised in a substantially pure form. An example for such a DNA is a suitable DNA sequence that has, for example, been obtained by using restriction endonucleases, so that they can further be manipulated according to the invention, for example, it can be amplified. Such a DNA is usually called a recombinant DNA. Thus, a suitable DNA comprises completely synthetic DNA, semi-synthetic DNA, DNA isolated from biological sources and DNA derived from introduced RNA. In general the introduced DNA is no original constituent of the genotype of the recipient DNA, but, according to the invention, also a gene can be isolated from a given genotype and can optionally be modified and, subsequently, multiple copies of the gene can be introduced into the same genotype, e.g. for enhancing the production of a given gene product.

The introduced DNA comprises without limitation DNA from genes, such as, for example, from bacteria, yeasts, fungi or viruses. The introduced DNA can comprise modified or synthetic genes, portions of genes or chimeric genes including genes of the same or a different genotype.

The DNA used according to the invention for transformation can be circular, linear, double-stranded or single-stranded. In general the DNA is present in form of a chimeric DNA, such as a plasmid DNA, also containing coding regions flanked by regulator sequences assisting in the expression of the recombinant DNA being present in the transformed cell. For example, the DNA itself can contain a promoter or can consist thereof, which is active in a cell, and which is derived from a source that is different to said cell, or a promoter can be used that is already present in the cell, i.e. the target cell for transformation.

In general the introduced DNA is relatively small, less than approximately 30 kb, in order to minimise the susceptibility vis-à-vis physical, chemical or enzymatic degradation increasing with the size of the DNA.

The selection of a suitable expression vector depends on the host cells. Expression vectors for yeast or fungi can comprise an origin of replication, a suitable promoter and enhancer but also any necessary ribosome-binding sites, polyadenylation sites, splice-donor and splice-acceptor sites, transcription termination sequences and non-transcribed 5'-flanking sequences.

Examples for suitable host cells are: fungal cells of the genus *Aspergillus, Rhizopus, Trichoderma, Neurospora, Mucor, Pencillium*, etc. such as, for example, yeasts of the genera *Kluyveromyces, Saccharomyces, Schizosaccharomyces, Trichosporon, Schwanniomyces, Hansenula, Pichia* and the like. Suitable host systems are, for example, fungi such as *Aspergilli*, e.g. *Aspergillus niger* (ATCC 9142) or *Aspergillus ficuum* (NRLL 3135) or *Trichoderma* (e.g. *Trichoderma reseei* QM6a) and yeasts such as *Saccharomyces*, e.g. *Saccharomyces cerevisiae* or *Pichia*, such as, for example, *Pichia pastoris* or *Hansenula*, e.g. *H. polymorpha* (DSMZ 70277). Such microorganisms can be obtained from recognised depositories, e.g. from the American Type Culture Collection (ATCC), the Centraalbureau voor Schimmelcultures (CBS) or the Deutschen Sammlung für Mikroorganismen und Zellkulturen GmbH (DSMZ) or any other depositories.

The expression cassette can contain in 5'-3'-transcriptional direction a transcription and translation initiation region of the polynucleotide according to the invention and a transcription and termination region, which is functional in vivo or in vitro. The termination region can be native as regards the transcription initiation region or can be native as regards the polynucleotide or can be of other origin. The regulator sequences can be localised upstream (5' non-coding sequences) within (intron) or downstream (3' non-coding sequences) of a coding sequence and can influence the transcription, the RNA processing or the stability and/or the translation of the associated coding sequence. Regulator sequences can, without limitation, comprise enhancers, promoters, repressor-binding sites, translation-leader sequences, introns or polyadenylation signal sequences. They can comprise natural and synthetic sequences as well as sequences that are a combination of synthetic and natural sequences.

The vector used according to the invention can also comprise suitable sequences for amplifying the expression.

Examples for promoters that can be used according to the invention are promoters of which is know that they control the expression in the eukaryotic cells. Any promoters having the capability for expression in filamentous fungi can be used. Examples are a promoter that is strongly induced by starch or cellulose, e.g. a promoter for glucoamylase or α-amylase from the genus *Aspergillus* or cellulase (cellobiohydrolase) from the genus *Trichoderma*, a promoter for enzymes in the glycolytic pathway, such as phosphoglycerat kinase (PGK) and glyceraldehyde-3-phosphate dehydrogenase (GPD), etc. The cellobiohydrolase I, the cellobiohydrolase II, the amylase, the glucoamylase, the xylanase or the enolase promoter is preferred.

Two main methods for controlling the expression are known, i.e. overexpression and underexpression. Overexpression can be achieved by insertion of one or more extra copies of the selected gene. For underexpression there are two main methods, which are usually designated as "anti-sense downregulation" and "sense downregulation" in the art. In general these methods are designated as "gene silencing". Both of these methods result in an inhibition of the expression of the target gene.

In addition to the use of a specific promoter, other types of elements can influence the expression of transgenes. It has especially been shown that introns have a potential for enhancing the transgene expression. The expression cassette can even comprise further elements, for example, those that can be regulated by endogenous or exogenous elements such as zinc finger proteins including naturally occurring zinc finger proteins or chimeric zinc finger proteins.

The expression cassette used according to the invention can further contain enhancer elements or upstream promoter elements.

Vectors for use according to the invention can be constructed as to obtain an enhancer element. The constructs according to the invention, thus, comprise the gene of interest together with a 3' DNA sequence acting as a signal for terminating the transcription and for allowing for polyadenylation of the thus obtained mRNA. Any signal sequences allowing for secretion from the chosen host organism can be used. The preferred signal sequence is the phytase signal sequence from *Aspergillus niger* or signal sequences derived from it for secretion from filamentous fungi.

A specific leader sequence can also be used, as the DNA sequence between the transcription initiation site and the beginning of the coding sequence, i.e. the non-translated leader sequence can influence gene expression. Preferred leader sequences comprise sequences controlling the optimal expression of the attached gene, i.e. they comprise a preferred consensus leader sequence increasing or maintaining mRNA stability and preventing an inappropriate translation initiation. The selection of such sequences is well known to a person skilled in the art.

A selectable or screenable marker gene can be introduced into the expression cassette for improving the possibility to identify the transformants. Such marker genes are well known to a person skilled in the art.

The expression cassette or a vector construct containing the expression cassette is introduced into a host cell. A plurality of techniques is available and well known to a person skilled in the art for introducing constructs into the host cell. The transformation of microbial cells can be carried out using polyethylene glycol, calcium chloride, viral infection, DEAE-dextran, phage infections, electroporation, and other methods known in the art. The transformation of fungi can be carried out according to Penttilä et al., Gene 61:155-164, 1987. The introduction of a recombinant vector in yeasts can be carried out according to methods known per se including electroporation, use of spheroplasts, lithium acetate and the like.

As soon as the expression cassette and DNA sequence, respectively, according to the invention is obtained, it can be inserted into vectors by methods known per se for overexpressing the encoded polypeptide in suitable host systems. However, DNA sequences can also be used as such for transforming suitable host systems of the invention for achieving overexpression of the encoded polypeptide.

As soon as a DNA sequence according to the invention has been expressed in a suitable host cell in a suitable medium, the encoded phytase can be concentrated and/or isolated according to methods known per se either from the medium, in case the phytase is secreted into the medium, or from the host organism, in case the phytase is present intracellularly, e.g. in the periplasmatic space. Known methods for separating the insoluble components of the culture medium and the biomass followed by methods for concentrating the phytase can be applied for the production of concentrated phytase solutions or as a preparation for drying the phytase. For example, filtration methods or centrifugation methods can be used for separating the insoluble components, followed by ultrafiltration methods for concentrating, or cross-flow filtration methods are applied. The drying can be carried out by lyophilisation or spray trying, granulation methods, extrusion or other methods. Known methods of protein purification can be applied for isolating the phytases according to the invention. For example, different chromatographic or gelchromatographic methods can be applied individually or in combination. Depending on the used host cell in a recombinant production method, the enzyme according to the invention can be modified or not covalently by glycosylation. In eukaryotic cells glycosylation of the secreted proteins serves for modulating the protein folding, the conformational stability, the thermal stability and the resistance vis-à-vis proteolysis. In view of a specific application of the phytase a glycosylated variant of the enzyme can be preferred over a non-glycosilated variant. For example, the use of a glycosylated phytase in animal feed serves for protecting the enzyme against thermal denaturation during feed pelletisation or against proteolytic inactivation upon passage through the animal stomach, whereby the distribution of the active enzyme in the intestinal tract and to the site of action is promoted. For uses in food processing, wherein the enzyme activity is only desired during processing and not in the end product, a phytase that is thermal-labile, i.e. non-glycosylated, and susceptible to proteolytic degradation, may be preferred.

The invention also relates to phytase compositions containing the polypeptide according to the invention. In general phytase compositions are liquid or dry. Liquid compositions contain the phytase enzyme preferably in a purified or enriched form. However, auxiliary agents such as, for example, a stabiliser with glycerol, Sorbitol or monopropylene glycol, additives like salts, sugar, preservatives, means for adjusting the pH value, proteins and phytate or salts of myoinositol phosphates (a phytase substrate) can be added. Typically liquid compositions are aqueous or oily suspensions or slurries, respectively. The liquid compositions can be added to a food or feed prior to or following a possible pelletisation or processing step. Dry compositions can be lyophilised, spray-dried or extruded compositions, which can exclusively contain the enzyme. Dry compositions can be granulates, which can easily be mixed with food or feed components, or, more preferably, form a component of a premix. The particle size of the enzyme granulate is preferable compatible to the other components of the mixture. This allows for save and convenient means for incorporating enzymes, for example, in processed food, premixes or animal feed.

A stable formulation of the phytase enzyme according to the invention can, for example, be produced by spraying a mixture of a liquid enzyme solution onto a bulking agent such as ground soy bean flour and then drying the mixture. The reduction of moisture and the binding interactions of the phytase with the bulking agent protect the enzyme of environmental influences such as extremata of temperature, which can occur during the production of feed. Dry and liquid formulations can be further stabilised when the activity of potential proteolytic enzymes is reduced, which can be present as biproducts in the liquid fermentation mixture used for the production of the enzyme according to the invention. The thus obtained dry enzyme mixture can be used as a feed supplement for use in poultry and pig breeding. For example, the addition of 250 enzyme units of the enzyme according to the invention to 1 kg of standard wheat diet shows similar effects as 500 enzyme units of *Aspergillus* phytase. Moreover, a reduction of the phosphate supplementation results in a decrease of the phosphate pollution, which in turn significantly reduces the environmental stress by intensive animal breeding.

As soon as a dry enzyme preparation is obtained, a agglomeration granulate can be produced. Therefore, a high-shear blender is used, whereby bulking agent and the enzyme coagglomerate and a granulate is formed. Absorption granulates are produced by coating cores of a supporting material by the enzyme according to the invention. Typical bulking materials are salt such as disodium sulfate. Other bulking materials comprise kaolin, talcum, magnesium aluminium silicate and cellulose fibres. Optionally, binding agents such as dextrines are also incorporated into the agglomeration granulate.

Typical supporting materials comprise starch, e.g. in the form of cassava, potato, cereals, in particular maize, rice and wheat or protein containing products such as e.g. soy proteins. Salts can also be used. Optionally the granulate is coated with a coating mixture. Such a granulate comprises coating agents, preferably hydrophobic coating agents, dehydrogenated palm oil and talcum and optionally other additives such as calcium carbonate or kaolin for improving the bioavailability at the intended site of action.

Additionally, the mixtures with phytase can contain other substances such as colouring agents, flavourings, stabilisers, vitamins, minerals, other food and feed enzymes and the like. This refers in particular for the so-called premixes.

A food or feed additive is an essentially pure compound or a composition of several compounds, which are intended for or suitable for addition to food or feed. Specifically, it is a substance that becomes a component of a food or a feed according to its intended purpose or influences the properties of a food or feed product. Thus, a phytase additive shall designate a phytase that is not a natural constituent of the substances mainly used for food and feed or is not present therein in a natural concentration. For example, the phytase is added to the feed separately from the feed substances alone or in combination with other feed additives. A typical premix usually comprises one or more compounds such as vitamins, minerals or feed-fortifying enzymes and suitable carriers and/or excipients.

A phytase additive ready-to-use is an additive that is not produced in situ in feed or in processed food. A phytase additive ready-to-use can be administered to humans or animals directly or preferably directly after blending with other components of feed or food. For example, a feed additive according to this aspect of the present invention is combined with other feed stuffs and feed additives for obtaining a premix or supplementary feed. Such other feed components comprise one or more other (preferably thermal stable) enzyme supplements, other feed additives, mineral feeds and amino acids. The thus obtained (combined) feed additives can comprise different types of compounds and can, then, be blended in their appropriate amount with feeds such as cereal and protein carriers for obtaining a combined animal feed. The processing of these components to animal feed can be carried out following blending with processing devices, which are known per se, such as a double pelletising machine, a steam pelletiser, an expander or an extruder.

Similarly, a food additive according to this embodiment of the present invention can be combined with other food components whereby processed food products are produced. Such other food components comprise one or more enzyme supplements, vitamins, minerals and trace elements. The thus obtained combined food supplement can be blended in an appropriate amount with other food components such as cereals and plant proteins for yielding a processed food. The processing of these compounds into a processed food can be carried out using processing devices that are known per se.

In a preferred embodiment the phytase compositions according to the invention comprise additionally an effective amount of one or more enzymes for food or feed, preferably selected from alpha-galactosidases, beta-galactosidases, laccases, other phytases, phosphatases, endoglucanases, especially endo-beta-1,4-glucanases, endo-beta-1,3(4)-glucanases, endo-1,2-beta-glucanases and endo-1,3-alpha-glucanases, cellulases, xylosidases, galactanases, especially arabinogalactanendo-1,4-beta-galactosidases and arabinogalactan-endo-1,3-beta-galactosidases, pectin degrading enzymes, especially pectinases, pectin esterases, pectinlyases, polygalacturonases, arabananases, rhamnogalacturonases, rhamnogalacturonanacetylesterases, rhamnogalacturonan-alpha-rhamnosidases, pectate lyases and alpha-galacturonidases, mannanases, especially beta-mannosidases, mannan acetylesterases, xylan acetylesterases, proteases, xylanases, arabinoxylanases and lipolytic enzymes such as lipases, phospholipases and cutinases.

The animal feed additive according to the invention is administered to the animal prior to or simultaneously with the feed. Preferably, the animal feed additive according to the invention is administered to the animal simultaneously with the feed.

An effective amount of phytase in food and feed is approximately 10-20,000 PPU/kg, preferably approximately 10-15,000 PPU/kg, more preferred approximately 10-10,000 PPU/kg, especially approximately 50-5,000 PPU/kg, in particular 50-2,000 PPU/kg feed or food.

The invention also relates to the use of phytase for processing and manufacturing food and feed. Cereals and flours for food can be treated enzymatically with phytase for reducing the phytine content or the raw materials. Reduced phytine contents improve food quality by increasing the availability of essential minerals such as iron, calcium and zinc. In addition to the increase of the quality of food, the use of phytase during processing can improve the total efficiency of food production. For example, the addition of phytase to white soy bean flakes during the production of a soy protein isolate can significantly increase yield and quality of the extractable protein. Thereby, the phytase is only active during production and processing, and is no longer active in the final product. This aspect is of importance in particular in the production of dough and in baking and in the production of other cereal-based ready-for-use food. Similarly, animal food components such as toasted soy bean flour or canola flour can be pretreated with phytase prior to the actual production process. The removal of anti-nutritive factors in animal food components prior to the production leads to a physiologically higher quality and to more valuable animal feed ingredients. In these processing methods the phytase is active during production and is usually no longer active in the digestive tract of the animal upon ingestion of the treated feed.

In addition to the use of phytase as an auxiliary means in feed processing the present invention also relates to the use of the phytase according to the invention as a digestion aid ("Verdauungshilfe"). Phytase in the form of tablets can be as taken in together with food intake for distributing the active enzyme in the gastro-intestinal tract.

The phytase according to the invention can advantageously be employed as well in monogastric as well as polygastric animals, especially in young calves. Feed for fish and shellfish ("Schalentiere") can also be supplemented with phytase for improving the exploitation of the food and for reducing the content of excreted phosphors in intensive animal breeding. The feed according to the invention can also be administered to animals such as poultry, e.g. poulardes, turkey hens, geese, ducks as well as pigs, horses, cattle, sheep, goats, dogs and cats as well as fish and shellfish. However, administering the feed according to the invention to pigs or poultry is particularly preferred.

Phytase formulations according to the invention can also be combined with other ingredients, whereby new and particularly advantageous feed compositions are created. As explained above, the availability of plant phosphate is low in soy bean flour and cereals due to binding to phytic acid. Thus, inorganic phosphate is added to feed for ensuring an adequate phosphorous supply of the animals. However, these feeds contain too much total phosphate and lead thus to a pollution of the environment with phosphate. Specifically, the animal feed according to the invention comprises the combination of a phytase according to the invention with animal feed ingredients in order to provide a feed containing essentially reduced contents of added inorganic phosphorous. In a preferred embodiment the feed according to the invention comprises typical feed ingredients, micro-nutrients, trace elements, vitamins, etc. as well as an effective amount of phytase and inorganic phosphorous, wherein the amount of the phytase of the phosphorous are between 50 and 20,000 units phytase/kg feed and less than 0.45% inorganic phosphorous, preferably between contents of 100-10,000 units phytase/kg feed and less than 0.225% inorganic phosphorous, in particular contents of 150-10,000 units phytase/kg feed and less than 0.15% inorganic phosphorous, in particular contents of 200-20,000 units phytase/kg feed and no additional inorganic phosphorous.

The invention also relates for improving the weight gain and the feed conversion ratio (FCR) in animal nutrition as well as the use of the phytase according to the invention in one of these methods. A phytase according to the invention allows for improved weight gains and an improved feed conversion ratio, in particular in association with feed having little inorganic phosphate. According to the methods of the invention the content of inorganic phosphate in feed can be reduced below contents of 0.45%, preferably below 0.225%. Preferably, no inorganic phosphate is added. By an increased phosphate availability due to the addition of the enzyme according to the invention, the bone mineralization of the animals can significantly be improved, which is in particular of importance in fast-growing animals.

According to another further embodiment the invention relates to the use of the enzyme according to the invention in baking, whereby development, elasticity and/or stability of the dough and/or the volume, the crump structure and/or the resistance of the baking good ("Backgut") to staling ("Altbackenwerden") is improved. Although the enzyme preparation according to the invention can be used for the production of dough or baked products of any type of flour, e.g. based on rye, barley, oats or maize, the enzyme preparation according to the invention has proven particularly useful in the production of dough or bakery products of wheat or of a substantially wheat proportion. The bakery products, which can be produced with an enzyme preparation according to the invention, comprise bread, rolls, baguette and the like. For baking the enzyme preparation according to the invention can be used with a further enzyme activity, such as, for example, xylanase, lipase, amylase, oxidase or laccase besides the phytase or can be used in combination with further enzymes such as lipase, amylase, oxidase (e.g. glucoseoxidase, peroxidase).

The following examples illustrate the invention in more detail.

EXAMPLE 1

Determination of Phytase Activity

The phytase activity was measured in an assay mixture of 0.5% phytic acid (approximately 5 mM), 200 mM sodium citrate, pH 5.0. After 15 minutes of incubation at 37° C. the reaction was stopped by adding one same volume 15% trichloracetic acid. The released phosphate ions were quantitatively determined at 820 nm by mixing 100 µl of the assay mixture with 900 µl $H_2O$ and 1 ml 0.6 M $H_2SO_4$, 2% ascorbic acid and 0.5% ammonium molybdate after incubation at 50° C. and a duration of 20 min. Potassium phosphate standard solutions were used a reference.

EXAMPLE 2

Construction of the Plasmids pKDa2 and pKDa4

The phytase-encoding sequence of *E. coli* (Dassà et al. 1990, J. Bacteriol. 172:5497-5500, accession no.: M58704) was generated and synthesised using the codon usage of *T. reesei* (http://www.kazusa.or.jp/codon). All synthesised fragments were sequenced and fragments with and without mutations were associated, whereby now phytase variants were produced. In one of the finally obtained variants the acid $Val^{200}$ (GTG) of the phytase gene was altered to $Tyr^{200}$ (TAC). This variant was called Da2. The non-mutated original polynucleotide ("Stammpolynucleotid") was called Da4. The mature *E. coli* phytase gene clones were amplified by PCr. The DNA sequence having the CAG (Gln) codon in position 1 comprises an open reading frame of 1,230 bp and encodes an enzyme having 410 amino acids (SEQ ID NO: 1/2).

The signal peptide (18 amino acids) of *A. niger* phytase (SEQ ID NO: 3/4) was used for secreting the *E. coli* phytase from *Trichoderma reesei*. The synthetic gene having the modified *A. niger* phytase signal sequence and the mature *E. coli* phytase sequence, which contains the mutation V200Y, was cloned into plasmid pUC18. The thus developed vector was called Da2pUC3 and was deposited according to the above conditions as DSM 16396. The deposited plasmid contains the DNA with the fungal codon usage with slight modifications according to the required cleavage sites for the restriction enzymes as can be taken from the following table 1:

TABLE 1

| | T. reesei | | synthetic phytase gene | |
|---|---|---|---|---|
| fungal usage | codon | frequency per thousand | number of triplets in the synthetic E. coli phytase gene | frequency per thousand in the synthetic E. coli phytase gene |
| Ala | GCC | 43.3 | 20 | 48.8 |
| Ala | GCT | 19.1 | 10 | 24.4 |
| Ala | GCG | 16.0 | 4 | 9.8 |
| Ala | GCA | 10.3 | 3 | 7.3 |
| Arg | CGC | 14.3 | 12 | 29.3 |
| Arg | CGT | 7.0 | 6 | 14.6 |
| Arg | CGA | 6.4 | 0 | 0.0 |
| Arg | AGG | 5.5 | 1 | 2.4 |
| Arg | CGG | 5.1 | 3 | 7.3 |
| Arg | AGA | 2.5 | 0 | 0.0 |
| Asn | AAC | 43.3 | 13 | 31.7 |
| Asn | AAT | 10.3 | 3 | 7.3 |
| Asp | GAC | 37.5 | 14 | 34.1 |
| Asp | GAT | 15.7 | 5 | 12.2 |
| Cys | TGC | 12.8 | 5 | 12.2 |
| Cys | TGT | 4.0 | 3 | 7.3 |
| Gln | CAG | 37.1 | 24 | 58.5 |
| Gln | CAA | 8.6 | 5 | 12.2 |
| Glu | GAG | 31.1 | 17 | 41.5 |
| Glu | GAA | 6.9 | 4 | 9.8 |
| Gly | GGC | 54.4 | 16 | 39.0 |
| Gly | GGT | 16.9 | 6 | 14.6 |
| Gly | GGA | 13.0 | 6 | 14.6 |
| Gly | GGG | 8.2 | 1 | 2.4 |
| His | CAC | 18.3 | 7 | 17.1 |
| His | CAT | 4.0 | 1 | 2.4 |
| Ile | ATC | 29.9 | 11 | 26.8 |
| Ile | ATT | 15.1 | 0 | 0.0 |
| Leu | CTG | 26.1 | 27 | 65.9 |
| Leu | CTC | 25.1 | 21 | 51.2 |
| Leu | CTT | 9.9 | 5 | 12.2 |
| Leu | TTG | 6.7 | 0 | 0.0 |
| Leu | CTA | 1.8 | 0 | 0.0 |
| Leu | TTA | 0.3 | 0 | 0.0 |
| Lys | AAG | 38.5 | 13 | 31.7 |
| Lys | AAA | 3.4 | 1 | 2.4 |
| Met | ATG | 18.8 | 5 | 12.2 |
| Phe | TTC | 21.3 | 7 | 17.1 |
| Phe | TTT | 13.5 | 4 | 9.8 |
| Pro | CCC | 23.3 | 14 | 34.1 |
| Pro | CCT | 15.0 | 9 | 22.0 |
| Pro | CCG | 13.4 | 6 | 14.6 |
| Pro | CCA | 7.1 | 0 | 0.0 |
| Ser | TCC | 21.6 | 8 | 19.5 |
| Ser | AGC | 21.3 | 9 | 22.0 |
| Ser | TCG | 19.3 | 5 | 12.2 |
| Ser | TCT | 14.0 | 4 | 9.8 |
| Ser | TCA | 6.4 | 0 | 0.0 |
| Ser | AGT | 4.1 | 0 | 0.0 |
| Thr | ACC | 29.0 | 18 | 43.9 |
| Thr | ACG | 20.6 | 10 | 24.4 |
| Thr | ACT | 14.0 | 5 | 12.2 |
| Thr | ACA | 6.3 | 0 | 0.0 |
| Trp | TGG | 17.6 | 8 | 19.5 |
| Tyr | TAC | 27.1 | 4 | 9.8 |
| Tyr | TAT | 9.0 | 1 | 2.4 |
| Val | GTC | 36.3 | 14 | 34.1 |
| Val | GTG | 14.8 | 5 | 12.2 |
| Val | GTT | 11.7 | 4 | 9.8 |
| Val | GTA | 2.2 | 0 | 0.0 |

In the plasmid pKDa2 (Tyr$^{200}$ mutant) the synthetic gene is flanked by a SacII restriction site 16 base pairs upstream of the start codon and by a BamHI restriction site immediately downstream of the stop codon. The 16 base pairs upstream of the start codon belong to the T. reesei cbhI promoter (Shoemaker et al., 1983, Bio/Technology 1, 691-696). The synthetic gene was cleaved with SacII and BamHI and was inserted in the SacII and BamHI cleavage sites following the T. reesei cellobiohydrolase I promoter in the plasmid pALK487 (WO 94/28117). This plasmid construct was called pKDa1. A blunt-ended 4.78 kb long EcoRI/SpeI fragment of the plasmid pALK424 (WO 93/24621) containing the amdS marker and the 3'-flanking cbhI sequences was cloned into the StuI cleavage site of pKDa1, whereby the phytase expression vector pKDa2 was obtained. Said vector was mapped by restriction endonucleases and the complete sequence of the synthesised fragment was confirmed by sequencing.

The construction of the expression vector kPDa4 (wild-type) was carried out analogously.

The expression cassettes isolated from plasmids pKDa2 and pKDa4, respectively, contain the following genetic material:

CbhI (cellobiohydrolase I) promoter: The 2.2 kb EcoRI/SacII fragment containing the cbhI promoter is derived from Trichoderma reesei QM6a. The promoter region also works as homologous DNA (together with the cbhI 3' fragment; see below) for controlling the integration of the transforming DNA into the cbhI locus.

Signal sequence: The signal peptide of A. niger phytase (SEQ ID NO: 3/4) was used for secreting E. coli phytase from Trichoderma reesei.

E. coli phytase gene: Synthetic E. coli phytase gene (SEQ ID NO: 1) including the modified A. niger phytase signal sequence for expression in T. reesei was fused between the cbhI promoter and the cbhI terminator.

cbhI terminator: the 0.75 kb long BamHI/StuI fragment containing the cbhI terminator was added subsequent to the E. coli phytase in order to ensure the termination of the transcription.

amdS gene: The gene including its promoter and its terminator was isolated from Aspergillus nidulans VH1-TRSX6 and encodes acetamidase (Hynes et al., 1983, Mol. Cell. Biol. 3: 1430-1439; Kelly and Hynes, 1985, EMBO J. 4: 475-47). Acetamidase allows the strain to grow using acetamide as the single nitrogen source, and this characteristic has been used for selecting the transformant. The 3.1 kb fragment (blunt-ended SpeI/BamHI) contains 1,007 bps of the promoter region, 1,897 bps of the coding region (including introns) and 183 bps terminator region of the amdS gene.

cbhI 3' fragment: The fragment (1.7 kb, BamHI/EcoRI, starting 1.4 kb after the stop codon of the gene) was isolated from T. reesei ALKO2466. The strain ALKO2466 is derived from the strain ALKO233 (Harkki et al., 1991, Enzyme Microb. Technol. 13: 227-233). The 3' fragment is used together with the promoter region for targeted integration of the phytase expression cassette into the cbhI locus by homologous recombination.

The construct was chosen for targeted finding and replacement of the single-copy gene cbhI, which is present in T. reesei RH3780d, for studying the effect of the mutation by a single copy of the gene.

EXAMPLE 3

Transformation of Trichoderma reesei with pKDa2 and pKDa4 for Obtaining Single-Copy Transformants T. reesei RH 3780d was separately transformed with the linearised expression cassettes isolated from the plasmids pKDA2 and pKDa4. The techniques for transforming and maintaining T. reesei were those according to Penttilä et al (1987, Gene 61: 155-164). The transformants were selected and purified twice by single-spore isolation. Those transformants having the highest secretion efficiency were selected from all transformants. These transformants with DNA from the plasmid pKDa2 were designated RH 31068 and RH 31069, transformants with DNA from pKDa4 were designated RH 31071-31075, and used for further characterisation.

EXAMPLE 4

Secretion of Phytase in Shaken Flasks

Transformants carrying the expression cassettes of pKDa2 and pKDa4, respectively, were grown in shaken flasks on cellulase-inducing medium having the following composition: milk protein concentrate Nutrica 2%, lactose 1%, DSG 1.5%, $KH_2PO_4$ 5%, $(NH_4)_2SO_4$ 0.5%, corn steep powder 0.5%, balance tap water, adjustment of the pH value prior to sterilisation to 5.3. The culture filtrates obtained after 6-days' growth were used for SDS-PAGE analysis and for determination of the phytase activity. The results showed that the highest phytase activities were observed in the culture medium with transformants containing the pKDa2 expression cassette. The activities set forth in table 2 below are maximal activities, which were obtained in the fermentation of the best transformants in the period of 6 days.

TABLE 2

Production of E. coli phytase by transformants containing either the pKDa2 or the pKDa4 expression cassette.

| strain | SDS-PAGE | Southern Blot analysis integration event | phytase cassette copy number | phytase PPU $g^{-1}$ | expression cassette |
|---|---|---|---|---|---|
| RH31068 | CBHI⁻ | cbhI locus | one copy | 417 | pKDa2 |
| RH31069 | CBHI⁻ | cbhI locus | one copy | 411 | pKDa2 |
| RH31071 | CBHI⁻ | cbhI locus | one copy | 188 | pKDa4 |
| RH31072 | CBHI⁻ | cbhI locus | one copy | 182 | pKDa4 |
| RH31073 | CBHI⁻ | cbhI locus | one copy | 171 | pKDa4 |
| RH31074 | CBHI⁻ | cbhI locus | one copy | 167 | pKDa4 |
| RH31075 | CBHI⁻ | cbhI locus | one copy | 158 | pKDa4 |
| RH3780d | CBHI⁺ | | | 0.7 | |

The above results show that the strains transformed with the expression cassette pKDa2 containing the $Tyr^{200}$ mutant exhibit the phytase secretion, which is approximately twice as high as that of the strains transformed with the E. coli wild-type sequence pKDa4.

EXAMPLE 5

Southern Blotting

The Southern Blot Analysis was performed on genomic DNAs, which were isolated from the host strain RH3780d and transformants of both constructs, for evaluating the integration result of the expression cassette into the genome. Following cleavage of the genomic DNA with EcoRI and screening with a 9.0 kb EcoRI fragment, a hybridising band at 9.0 kb was pre-sent in all transformants. The size of that band corresponded with the 9.0 kb fragment of the expression cassette suggesting an intact integration of the complete cassette into the genome.

The cleavage of the DNA with XbaI showed two hybridising bands at 1.7 and 9.0 kb in the host strain, whereas three hybridising bands at 1.7, 4.0 and 7.0 kb were present in all transformants. As expected from the double crossing-over event, an integration of a copy of the expression cassette into the cbhI locus leads to three bands of 1.7, 4.0 and 7.0 kb and in absence of the 9.0 kb wild-type band. The 4.0 as well as the 7.0 bands replace the 9.0 band of the cbhI locus of the host and the 1.7 kb band was unchanged.

The intensities of the hybridised signals do not differ between the transformants and those constructs.

The results of the Southern Blotting analysis, SDS-PAGE and determination of the phytase activities are shown in table 2 above. The Southern Blot analysis showed that all selected transformants contained the E. coli phytase gene and the mutated gene, respectively, as single copy in the cbhI target locus.

EXAMPLE 6

Biochemical Characterisation of the Phytase Variants

Supernatants from recombinant strains were separated on NuPage BisTris 10% SDS-PAGE gel and stained with Coomassie (FIG. 1). Due to the glycosylation by the host strain the phytase occurred as three bands between 44.2 and 53.2 kDa. All samples were applied with equal phytase activities. The gels were dried and scanned on an Agfa flat bed scanner with the Phoretix ID Advanced software. The areas of the three bands were integrated and the data is summarised in the following table 3. For all four tested strains the sum of the area of all three phytase bands in equal within the scope of the measurement accuracy. This shows that the mutation in Da2 does not result in alterations in the specific activity of the enzyme and thus demonstrates that the mutation is responsible for the increased secretion of the phytase protein.

TABLE 3

Integration of the area of the phytase bands on the SDS-PAGE gel using the program Phoretix ID Advanced

| band | MW | RH 31074 (pKDa 4) lane 2 | RH 31071 (pKDa 4) lane 3 | RH 31069 (pKDa 2) lane 4 | RH 31068 (pKDa 2) lane 5 |
|---|---|---|---|---|---|
| 1 | approx. 50, 52.3 kDa | 56676016 | 52581584 | 42442918 | 41508017 |
| 2 | approx. 46.7, 48.8 kDa | 35235004 | 34577257 | 47107624 | 43668804 |
| 3 | approx. 44.2, 45.6 kDa | 18121276 | 16714340 | 15716570 | 13439975 |
| sum | | 110032296 | 103873181 | 105267112 | 98616796 |
| total protein/lane [ug] | | 2.04 | 1.49 | 0.85 | 0.78 |

EXAMPLE 7

Improvement of the Availability of Phosphate by the Phytase According to the Invention (Tyr$^{200}$ Mutant) in Pigs A digestion experiment was carried out with pigs in two sub-sequent collection periods of 5 days following an conditioning period of 9 days in each case. A ration with reduced content of digestible phosphate based on maize grist and extracted soy bean grist was used as a negative control and was supplemented with the phytase according to the invention (E. coli phytase mutant Tyr$^{200}$) in amounts of 125, 250, 500 and 750 PPU/kg feed. The phytase was added to the whole feed via a premix. In total 40 male castrated pig in 5 treatment groups were used. All treatment groups consisted of 8 pigs (4 pigs in two subsequent collection periods). The treatments were as follows:

negative control[1] (NC)
[1]feed: 71.5% maize flour, 28.8% extracted soy bean grist
NC+phytase (125 PPU/kg$^{-1}$)
NC+phytase (250 PPU/kg$^{-1}$)
NC+phytase (500 PPU/kg$^{-1}$)
NC+phytase (750 PPU/kg$^{-1}$)
4.4 g kg$^{-1}$ total P; 1.9 g kg$^{-1}$ non-phytate P; 5.5 g kg$^{-1}$ Ca; native phytase: 90 PPU/kg$^{-1}$.

The measured parameters comprise phosphate and calcium digestibility as well as phosphate and calcium retention.

Phosphate Retention and Excretion:

The results show that the phosphate digestibility was significantly increased by 42.5% in the negative control to 59.3, 65.3, 65.0 and 66.3%, respectively, (p<0.05) at all added amounts of phytase (125; 250; 500 and 750 PPU/kg$^{-1}$ feed). This led to a significant decrease of the faecal phosphate excretion of 203 mg kg$^{-1}$ 0.75 d$^{-1}$, measured in the negative control group, to 142, 120, 121 and 116 mg kg$^{-1}$ 0.75 d$^{-1}$ in the treatment groups with phytase-enriched feed (p<0.05). The phosphate retention improved significantly from 152 mg kg$^{-1}$ 0.75 d$^{-1}$, measured in the negative control, to 221, 232, 231 and 236 mg kg$^{-1}$ 0.75 d$^{-1}$ in the treatment groups with phytase-enriched feed (p<0.05). The differences between the phytase treatments were significant between the lowest dosage (125 PPU kg$^{-1}$ feed) and all other administrations (p<0.05).

Calcium Retention and Excretion

The addition of phytase according to the invention increased the calcium utilisation significantly (p<0.05) by 12.1, 14.3, 15.2 and 14.6% as compared to the control group. The calcium excretion via the urine was relatively high (114 mg kg$^{-1}$ 0.75 d$^{-1}$) in the negative control, which was presumably to ascribe to the low P content in the feed. The calcium excretion via the urine was reduced to 108, 118, 95 and 88 mg kg$^{-1}$ 0.75 d$^{-1}$ in the phytase treatment groups, which was significant for the highest amount administered (750 PPU kg$^{-1}$, p<0.05) as compared with the negative control. The calcium retention measured in the negative control was significantly (p<0.05) increased from 181 mg kg$^{-1}$ 0.75 d$^{-1}$ to 240, 245, 266 and 270 mg kg$^{-1}$ 0.75 d$^{-1}$ by all phytase treatments. The differences between the added amounts of phytase were significant (p<0.05) between the higher dosages (500 and 750 PPU kg$^{-1}$ feed) as compared to the lower dosages (125 and 250 PPU kg$^{-1}$).

The results show that the phytase according to the invention had a good effect on the degradation of phytate in the digestive tract of pigs. Low amounts of the phytase according to the invention can already promote the calcium and phosphate digestibility and retention in a similar extent as higher added amounts.

EXAMPLE 8

Improvement of the Availability of Phosphate by the Phytase According to the Invention (Tyr$^{200}$ Mutant) in Poulardes A digestion experiment was carried out with poulardes ("Masthühner") in two collection periods. One collection period of 4 days was carried out following a conditioning period to the cages of also 4 days. The collection periods were carried out at the end of the starter phase and at the end of the growth phase. A ration with reduced content of digestible phosphate, based on maize grist and extracted soy grist, was used as a negative control and was supplemented with the phytase according to the invention in amounts of 125 and 250 PPU kg$^{-1}$ feed. Additionally, a further treatment was carried out with the recommended phosphate content without phytase addition. In total 24 male poulardes were assigned to 4 treatment groups. The treatment groups consisted of 6 poulardes per collection period. The treatment were as follows:

negative control[1] (NC)
[1]Feed: 53.6-56.5% maize flour; 37.9-34.5% extracted soy bean grist; 4.4-4.7 g kg$^{-1}$ total P; 2.0 g kg$^{-1}$ non-phytate P; 6.4-5.9 g kg$^{-1}$ Ca
NC+phytase (125 PPU kg$^{-1}$)
NC+phytase (250 PPU kg$^{-1}$)
positive control[2]
[2]Feed: 50.4-54.3% maize flour; 35.9-35.0% extracted soy bean grist; 7.3-6.4 g kg$^{-1}$ total P; 4.5-3.5 g kg$^{-1}$ non-phytate P; 9.8-7.8 g kg$^{-1}$ Ca The measured parameters comprise phosphate excretion and phosphate retention. The results show that both added amounts of phytase P (125 and 250 PPU kg$^{-1}$ feed) increased the phosphate retention and decreased the phosphate excretion. The measurements at the end of the start phase showed a significant increase of the phosphate retention from 58.7% in the negative control to 64.2 and 63.9% for the phytase treatment (p<0.05). This led to a reduction of the phosphate excretion in poulardes having received the phytase, which was reduced by 11.4 and 12.7% (tendency) as compared to the negative control. Measurements at the end of the growth phase also showed an increase of the phosphate retention from 54.7% in the negative control to 58.2 and 58.9% for phytase treatments (tendency). This led to a decrease of the phosphate excretion in poulardes having received the phytase, which was significantly (p<0.05) reduced by 11% and 12.7% as compared to the negative control.

EXAMPLE 9

Baking Experiment: Vienna Bread

Vienna bread was baked of 320 g dough pieces obtained by mixing 1,000 g wheat flour (Pfälzer Mühlenwerke, Mannheim, Type 550), 30 g compressed yeast (Fala GmbH, Germany), 20 g salt, 50 mg ascorbic acid, 580 g water. After mixing of all ingredients at slow speed for 2 minutes and mixing for 6 minutes at high speed (Diosna SP12 Mixer), the dough had a temperature of 27° C. and was left for 10 minutes at ambient temperature (22° C.) below a cloth covering. Following the first dough rest period, the dough was partitioned into pieces of 320 g each (±1 g tolerance) and was shaped to a round form. Thereafter, a second dough rest period of 20 minutes followed. Following the second dough rest period, the dough was formed in a mechanical device and was placed on fermentation plates covered with cloth. The bread dough was then fermented at 32° C. under 85% relative humidity (final maturation) and was baked after a maturation time of 70 minutes. The dough/the bread was baked with a 5-seconds' steam injection for 35 minutes at 235° C. in and oven having multiple insertion levels ("in einem mehrschienigen Ofen") (Winkler & Wachtel, Germany).

The different effects of the phytase according to the invention (E. coli phytase mutant Tyr$^{200}$) in the baking experiments were compared with a control dough without phytase addition in parallel. The volume of the control breads was taken for 100%.

The volume of the bread loaves was determined by the rape seed displacement method ("Rapssamenverdrängungsverfahren"). The dough rheology and the bread properties were evaluated sensorically by a qualified application specialist/test baker and the average volume of three loaves per test was measured.

The results of the baking experiment are summarised in the following table 4:

TABLE 4

| experiment | | | | | | | | | | | |
|---|---|---|---|---|---|---|---|---|---|---|---|
| units per kg flour | | | | | | | | | | | |
| | 0 | 110 | 220 | 430 | 870 | 1730 | 3460 | 6930 | 13860 | 27715 | 55430 |
| dough after pasting ("Anteigen") | | | | | | | | | | | |
| strength | 4 | 4.5 | 4.5 | 5 | 5 | 5 | 5 | 5 | 6 | 6 | 6 |
| dough after final proofing ("End-gare") | | | | | | | | | | | |
| volume | 4 | 4 | 4 | 4 | 4 | 4 | 4 | 4 | 4 | 4 | 4 |
| stability | 4 | 4 | 4 | 5 | 5 | 5 | 5 | 5 | 5.5 | 5.5 | 5.5 |

Evaluation Criteria:

| evaluation criteria | 1 | 2 | 3 | 4 | 5 | 6 | 7 |
|---|---|---|---|---|---|---|---|
| dough after pasting | | | | | | | |
| strength | much softer | softer | slightly softer | as reference | slightly firmer | firmer | much firmer |
| dough after final proofing | | | | | | | |
| volume | much smaller | smaller | slightly smaller | as reference | slightly larger | larger | much larger |
| stability | very unstable | unstable | slightly unstable | as reference | slightly more stable | more stable | much more stable |

Explanation of the Evaluation Criteria:
Strengths: stiffness of the dough, evaluated by an experienced baker.
Volume: visual evaluation of the volume of the piece of dough ("Teigling") after final proofing.
Stability: test of the gas retention capability by pressurisation of the piece of dough after final proving and evaluation of the decreased volume, which has occurred.

The above results show that the phytase according to the invention had a stabilising effect on the dough.

The phytase according to the invention had a stabilising effect on the dough.

The experiments according to Examples 7 to 9 show that the E. coli phytase mutant Tyr$^{200}$ according to the invention is not different from the wild-type phytase in its effect. However, the E. coli phytase mutant Tyr$^{200}$ according to the invention is characterised by the advantage of a higher activity in the culture supernatant in total and a higher secretion efficiency, respectively, as compared to the wild-type.

EXAMPLE 10

Construction of the Plasmid pKDa41

The plasmid pKDa41 comprises the E. coli phytase gene (WT) under control of the T. reesei cbhI promoter and the cbhI terminator. The construction is comparable to the construction of the plasmid pKDa4 with the exception that the 16 base pairs upstream to the phytase start codon CCGCGGACTGCGCATC ATG (SEQ ID NO: 5) were altered to CCGCGGACTAGGCATC ATG (SEQ ID NO: 6) and a PacI restriction site was localised immediately downstream of the stop codon.

For constructing the plasmid pKDa41 the E. coli phytase gene (WT) was amplified from the plasmid pKDa4 via PCR. The PCR product was cleaved with AvrII and PacI and was inserted into the SpeI and PacI cleavage sites following the T. reseei cbhI promoter in the plasmid pAB489. The resulting plasmid has the designation pKDa41 and was mapped by restriction endonucleases and the phytase sequence was confirmed by sequencing. The expression cassette (NotI fragment) isolated from the plasmid pKDa41 contains identical genetic materials such as those from the plasmid pKDa4. The plasmid pKDa41 was used as starting material for reducing diverse phytase variants and as a reference in the examination of the phytase expression in T. reesei RH3780d.

The plasmid pAB489 results from the plasmid pALK487 (WO 94/28117) by insertion of further restriction sites (SpeI and PacI) into the SacII site between the cbhI promoter and the cbhI terminator contained in pALK487 as well as the 4.78 kb long EcoRI/SpeI fragment of the plasmid pALK424 (WO 93/24621) presented in Example 2 and containing the amdS marker and the 3' flanking cbhI sequences. The positioning of the elements is the same as in pKDa4 and allows for the direct cloning of the gene variants in to the SpeI and PacI cleavage sites of the multicloning site following the T. reesei cbhI promoter.

EXAMPLE 11

Construction of the Phytase Variant Plasmids

The following phytase variant plasmids were constructed: pPhy-V200L, pPhy-V200P, pPhy-L207F For producing the phytase variants the mutations of the phytase gene were carried out by the PCR method analogously to the principle that is reported in Nucleic Acids Research 1989, 17(2), 723-733 and Nucleic Acids Research 1990, 18(6), 1656. The construction as well as the cloning of the phytase variant plasmids are identical to the production of the plasmid pKDa41 reported in Example 10. The sequences of the phytase variants were confirmed by sequencing.

EXAMPLE 12

Transformation of *T. reesei* RH3780d with pKDa41 and Variants, Respectively The transformation of *T. reesei* RH3780d with the expression cassettes isolated from the plasmid pKDa41 of Example 10 and the phytase variant plasmids of Example 11 was carried out analogously to the transformation with the expression cassettes isolated from the plasmids pKDa2 and pKDa4 (Example 3). The expression cassettes were isolated as NotI fragments from the plasmids pKDa2, pKDa4, pKDa41 and phytase variant plasmids.

EXAMPLE 13

Production of *E. coli* Phytase by pKDa41 and Phytase Variant Expression Cassettes in Shaken Flasks The transformants were grown as described in Example 4 and the phytase in the culture filtrates was used for further examinations.

TABLE 5

Production of *E. coli* phytase by transformants containing either the pKDa41 or phytase variant expression cassettes.

| strain | SDS-PAGE | phytase cassette number of copies | phytase PPU $g^{-1}$ | expression cassette |
|---|---|---|---|---|
| RH31551 | CBHI⁻ | one copy | 82 | pKDa41 |
| RH31549 | CBHI⁻ | one copy | 76 | pKDa41 |
| RH31565 | CBHI⁻ | one copy | 225 | pPhy-V200L |
| RH31567 | CBHI⁻ | one copy | 230 | pPhy-V200L |
| RH31570 | CBHI⁻ | one copy | 291 | pPhy-V200P |
| RH31571 | CBHI⁻ | one copy | 295 | pPhy-V200P |
| RH31559 | CBHI⁻ | one copy | 114 | pPhy-L207F |
| RH31563 | CBHI⁻ | one copy | 112 | pPhy-L207F |
| RH3780d | CBHI⁺ | | 0.7 | |

---

The invention claimed is:

1. A recombinant DNA molecule which, upon expression in a prokaryotic or eukaryotic host cell, encodes a polypeptide having phytase activity, wherein the recombinant DNA molecule comprises a DNA sequence selected from
   a) DNA sequences which have been obtained by variations of the mature wild-type *E. coli* phytase sequence, wherein the mature wild type *E. coli* phytase sequence corresponds to SEQ ID NO: 8, and wherein an amino acid at position 200 or position 207 is mutated as compared to the wild-type sequence, or
   b) DNA sequences which are related to the sequences according to a) due to the degeneracy of the genetic code,
   wherein the recombinant DNA molecule is, upon expression in a suitable host cell, associated with an increased activity of the thus encoded protein in the culture supernatant.

2. The DNA sequence according to claim 1, wherein the mutation is selected from Val 200→Leu, Val 200→Ile, Val 200→Pro, Val 200→Tyr, or Leu 207→Phe.

3. The recombinant DNA molecule according to claim 1 wherein the molecule consists of SEQ ID NO: 7.

4. A DNA construct having the capability to control the expression of a mutated phytase gene in a host upon introduction in a suitable host cell, wherein the construct comprises optionally a promoter, optionally signal- and marker sequences, a DNA sequence according to claim 1, a terminator and optionally 5'- and 3'-flanking sequences.

5. The DNA construct according to claim 4, wherein the promoter is the cellobiohydrolase I, the cellobiohydrolase II, the amylase, the glucoamylase, the xylanase or the enolase promoter.

6. The DNA construct according to claim 4, wherein the signal sequence is an optionally modified phytase signal sequence from *Aspergillus niger*.

7. A vector having the capability to transform a host cell, wherein the vector comprises a construct according to claim 4.

8. The vector according to claim 7, wherein the plasmid corresponds to the plasmid Da2pUC3, deposited under the accession number DSM 16396.

9. A transformed host cell, selected from fungus, yeast, bacteria and mammalian cells, comprising a recombinant DNA molecule according to claim 1 and being capable to express a polypeptide having phytase activity.

10. The transformed host cell according to claim 9, wherein the host cell belongs to the genus *Aspergillus, Rhizopus, Trichoderma, Neurospora, Mucor* or *Penicillium*.

11. A method for producing phytase, wherein a transformed host cell according to claim 9 is grown under conditions conductive to the formation of phytase, and the thus produced phytase is isolated.

* * * * *